(12) United States Patent
Denes et al.

(10) Patent No.: US 9,107,858 B2
(45) Date of Patent: Aug. 18, 2015

(54) DENDRITIC CELL TARGETING COMPOSITIONS AND USES THEREOF

(75) Inventors: Ferencz S. Denes, Madison, WI (US); Zsuzsanna Fabry, Madison, WI (US); Matyas Sandor, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1502 days.

(21) Appl. No.: 11/999,509

(22) Filed: Dec. 5, 2007

(65) Prior Publication Data

US 2010/0278919 A1    Nov. 4, 2010

(51) Int. Cl.
*A61K 39/00* (2006.01)
*A61K 39/38* (2006.01)
*C07K 16/28* (2006.01)

(52) U.S. Cl.
CPC ............. *A61K 39/00* (2013.01); *A61K 39/0005* (2013.01); *A61K 2039/5154* (2013.01); *C07K 16/28* (2013.01)

(58) Field of Classification Search
None
See application file for complete search history.

(56) References Cited

U.S. PATENT DOCUMENTS

| | | | |
|---|---|---|---|
| 6,165,440 A | 12/2000 | Esenaliev | |
| 7,128,816 B2 | 10/2006 | Denes et al. | |
| 2004/0022840 A1 | 2/2004 | Nagy et al. | |
| 2005/0266090 A1 | 12/2005 | Prokop et al. | |
| 2006/0199770 A1* | 9/2006 | Bianco et al. | 514/17 |
| 2006/0233712 A1* | 10/2006 | Penades et al. | 424/9.34 |
| 2006/0275371 A1 | 12/2006 | Dai et al. | |
| 2007/0148095 A1 | 6/2007 | Chen et al. | |
| 2007/0264199 A1 | 11/2007 | Labhasetwar et al. | |

FOREIGN PATENT DOCUMENTS

| | | |
|---|---|---|
| DE | 10 2004 036780 | 3/2006 |
| WO | WO 2006/007514 | 1/2006 |
| WO | WO 2007/105171 | 9/2007 |

OTHER PUBLICATIONS

Pantarotto et al., 2003, Chem and Biol. vol. 10: 961-966.*
Cinke et al., 2002, Chem Phys. Lett. vol. 365: 69-74.*
Kwon et al., 2005, PNAS, vol. 102: 18264-18268.*
Ma et al., 2004, J. Biomater. Sci. Polymer Edn. vol. 15: 1033-1049.*
Ma et al., Jun. 2006, JMEPEG. vol. 15: 376-382.*
Park et al., 2009, Int. Immunopharm. vol. 9: 1530-1539.*
Labrecque et al., 1993, Cancer Res. vol. 53: 3468-71.*
Denes, F et al. 2003 Dense medium plasma synthesis of carbon/iron-based magnetic nanoparticles system. J Applied Physics 94(5): 3498-3508.
Helm, E. 2007 Nanotechnology may replace existing treatments for cancer. Eukaryon 3:55-62.
Gould, P. 2006 Nanomagnetism shows in vivo potential. Nanotoday 1(4):34-39.
Jain, K. 2005 Nanotechnology-based drug delivery for cancer. Technology in Cancer Research & Treatment 4(4):407-416.
Alper, J. 2006 Nanotechnology driving big advances in cancer imaging. NCI Alliance for Nanotechnology in Cancer. website: http://nano.cancer.gove/news_center/monthly_feature_2006_apr.asp (accessed Mar. 15, 2007).
Kostarelos, K et al. 2007 Cellular uptake of functionalized carbon nanotubes is independent of functional group and cell type. Nature Nanotechnology 2:108-113.
Ma et al. 2004 Plasma synthesis of carbon magnetic nanoparticles and immobilization of doxorubicin for targeted drug delivery. J. Biomater Sci. Polymer Edn. 15(8):1033-1049.
Ma et al. 2006 Plasma synthesis of carbon-iron magnetic nanoparticles and immobilization of doxorubicin for targeted drug delivery. Journal of Materials Engineering and Performance 15(3):376-382.
Mönch et al. 2005 Ferromagnetic filled carbon nanotubes and nanoparticles: synthesis and lipid-mediated delivery into human tumor cells. Journal of Magnetism and Magnetic Materials 290-291:276-278.
International Search Report and Written Opinion for PCT/US2008/085258 dated Apr. 1, 2009.
International Preliminary Report on Patentability for Intl. Pat. Appln. No. PCT/US2008/085258, dated Jun. 17, 2010.
Wang, et al., "Size-dependent Endocytosis of Gold Nanoparticles Studied by Three-dimensional Mapping of Plasmonic Scattering Images," 8 J. Nanobiotech. 33, 1-13 (2010).
Zhang, et al., "Size-dependent Endocytosis of Nanoparticles," 21 Adv. Mater. 419-424 (2009).
Gratton, et al., "The Effect of Particle Design on Cellular Internalization Pathways" 105 (33) PNAS 11613-11618 (2008).
Chithrani, et al., "Determining the Size and Shape Dependence of Gold Nanoparticle Uptake in Mammalian Cells," 6(4) Nano Lett. 662-668 (2006).

* cited by examiner

*Primary Examiner* — Amy Juedes
(74) *Attorney, Agent, or Firm* — Foley & Lardner LLP

(57) ABSTRACT

The present invention provides compositions and methods for targeting dendritic cells of the immune system. In particular, the compositions comprise carbon nanoparticles, optionally magnetic carbon nanoparticles comprising iron, which are preferentially endocytosed by dendritic cells compared to macrophages when contacted with a biological sample. The nanoparticles of the present invention may be functionalized to enhance delivery of biomolecules to dendritic cells.

14 Claims, 8 Drawing Sheets resting anti-HEL T cells
(CD62 high, CD69 low)

activated anti-HEL T cells
(CD62 low, CD69 high)

DENDRITIC CELL TARGETING COMPOSITIONS AND USES THEREOF

GOVERNMENT SUPPORT

The invention was made with United States government support awarded by the following agency: NIH AIO46430. The United States government has certain rights in this invention.

FIELD OF THE INVENTION

The present invention relates generally to diagnostic and therapeutic applications of carbon nanoparticles. In particular, the present invention relates to carbon nanoparticles that selectively target dendritic cells of the immune system and may be used to monitor, isolate, and manipulate such cells. The present invention also relates to the use of carbon nanoparticles to deliver compounds to dendritic cells, including vaccines and therapeutic agents.

BACKGROUND OF THE INVENTION

The following description is provided to assist the understanding of the reader. None of the information provided or references cited is admitted to be prior art to the present invention.

The basis of acquired, specific immunity in an organism is the ability to discriminate between self and non-self antigenic substances. The mammalian immune system uses cell surface molecules known as the major histocompatibility complex (MHC) to discriminate between self- and non-self antigens. In the case of bacterial infections or other insults from external sources, new proteins or compounds enter the organism. Some cells involved in the immune response are capable of phagocytosing foreign organisms or proteins. These immune cells degrade the protein products and the derived peptides are expressed at the cell surface in association with MHC molecules, where a specific adaptive immune response is generated against novel non-self components. This activity is called antigen processing and presentation and cells that mediate this activity are called antigen presenting cells (APCs).

In addition to recognizing insults from external sources, the immune system is also designed to detect internal insults, e.g., cancer. Cancer cells express aberrant molecules known as tumor-associated antigens (TAAs). The immune system has the potential to recognize such structures as "foreign" and to mount specific immune responses against them, so as to reject tumor cells in much the same way as bacterial cells. Although a large number of human TAAs have been characterized, most of these antigens are also expressed by some normal cells. As a result, immunological tolerance to such molecules develops, making it difficult to stimulate responses against tumor-associated antigens. Moreover, induction of strong immune responses against self molecules may result in the development of autoimmune disorders.

APCs, such as dendritic cells (DCs) and macrophages, play important roles in the activation of innate and adaptive immunity as well as in the maintenance of immunological tolerance. Major efforts have been made to develop vaccines, in particular tumor vaccines, in an attempt to promote DC maturation and co-stimulation as a means of enhancing immunity. DC maturation serves as the critical switch from the maintenance of self-tolerance to the induction of immunity. Mature DCs stimulate cytotoxic T-lymphocyte (CTL) responses against cells expressing the antigen.

DCs are professional antigen-presenting cells having a key regulatory role in the maintenance of tolerance to self-antigens and in the activation of innate and adaptive immunity (Banchereau et al., 1998, *Nature* 392:245-52; Steinman et al., 2003, *Annu. Rev. Immunol.* 21:685-711). When DCs encounter pro-inflammatory stimuli such as microbial products, the maturation process of the cell is initiated by up-regulating cell surface-expressed antigenic peptide-loaded MHC molecules and co-stimulatory molecules. Following maturation and homing to local lymph nodes, DCs establish contact with T cells by forming an immunological synapse, where the T cell receptor (TCR) and co-stimulatory molecules congregate in a central area surrounded by adhesion molecules (Dustin et al., 2000, *Nat. Immunol.* 1:23-9). Once activated, CD8+ T cells can autonomously proliferate for several generations and acquire cytotoxic function without further antigenic stimulation (Kaech et al., 2001, *Nat. Immunol.* 2:415-22; van Stipdonk et al., 2001, *Nat. Immunol.* 2:423-9). It has therefore been proposed that the level and duration of peptide-MHC complexes (signal 1) and co-stimulatory molecules (signal 2) provided by DCs are essential factors in determining the magnitude and fate of an antigen-specific T cell response (Lanzavecchia et al., 2001, *Nat. Immunol.* 2:487-92; Gett et al., 2003, *Nat. Immunol.* 4:355-60). Thus, DCs play a significant role in mediating immune responses.

SUMMARY OF THE INVENTION

In one aspect, the present invention provides a vaccine delivery system comprising a carbon nanoparticle that is preferentially endocytosed by dendritic cells as compared to macrophages, and an antigen conjugated to the nanoparticle, wherein the antigen is capable of inducing a specific T cell response. In one embodiment, the carbon nanoparticle is a magnetic carbon nanoparticles. For example, the magnetic carbon nanoparticles may comprise iron in a concentration from about 0.5% to about 2%.

In one embodiment, the carbon nanoparticles, which are preferentially endocytosed by dendritic cells as compared to macrophages, have a diameter from about 30 to about 70 nm. In further embodiments, the nanoparticles may be conjugated to an antibody to facilitate the uptake of the nanoparticles by dendritic cells. In particular, the nanoparticles may be conjugated to antibodies which bind molecules on the surface of dendritic cells. For example, the antibody may be an anti-DC-SIGN antibody, an anti-DEC-205 antibody, or an anti-MR antibody.

In one embodiment, the antigen of the vaccine delivery system is associated with an infectious disease. For example, the infectious disease may be caused by a pathogenic microorganism such as a virus, a bacterium, a fungus or a protozoan. In a particular embodiment, the antigen is encoded by a viral gene. For example, the viral gene may be derived from a virus selected from the group consisting of a hepatitis B virus, a hepatitis C virus, a human immunodeficiency virus, a papillomavirus, and a herpesvirus. Examples of viral genes include, but are not limited to, a hepatitis B virus e antigen gene, a hepatitis B virus surface antigen gene, a hepatitis B virus core antigen gene, human immunodeficiency virus Env gp160 gene, Gag gene, Pol gene, Rev gene, Tat gene, Vif gene, and Nef gene.

In another embodiment, the antigen of the vaccine delivery system is a tumor-associated antigen. For example, the tumor-associated antigen may be an overexpressed tumor-associated antigen, a testis-tumor antigen, a mutated tumor-associated antigen, a differentiation tumor-associated antigen tyrosinase, MART, trp, MAGE-1, MAGE-2, MAGE-3, gp100, HER-2, Ras, PSA BCR-ABL, CASP, CDK, Ras, p53, HER-2/neu, CEA, MUC, TW1, PAP, survivin, telomerase, EGFR, PSMA, PSA, PSCA, tyrosinase, MART, TRP, gp100, MART, MAGE, BAGE, GAGE, LAGE/NY-ESO, RAGE, SSX-2, CD19, or CD20. In one embodiment, the antigen is conjugated to the nanoparticle via an amine functionality.

In one aspect, the present invention provides a method for inducing an immune response in a mammalian subject comprising administering to the subject a vaccine delivery system comprising a carbon nanoparticle that is preferentially endocytosed by dendritic cells as compared to macrophages, and an antigen conjugated to the nanoparticle, wherein the antigen is capable of inducing a specific T cell response. In one embodiment, the vaccine delivery system is administered subcutaneously or intravenously.

In one aspect, the present invention provides a method for isolating dendritic cells from a mammalian subject comprising administering to the subject magnetic carbon nanoparticles, wherein the nanoparticles are preferentially endocytosed by dendritic cells as compared to macrophages; isolating a blood or tissue sample from the subject; applying a magnetic field to the sample; and separating the dendritic cells by the magnetic field. In particular embodiments, the magnetic carbon nanoparticles comprise iron with a concentration from 0.5 to 2%.

In one aspect, the present invention provides a method for isolating dendritic cells from a sample comprising: contacting the sample with magnetic carbon nanoparticles, wherein the nanoparticles are preferentially endocytosed by dendritic cells as compared to macrophages; applying a magnetic field to the sample to capture the nanoparticles; and separating the dendritic cells having the endocytosed nanoparticles from the sample.

In one aspect, the present invention provides a method of treating a disorder of the immune system comprising: administering to a subject having a disorder of the immune system magnetic carbon nanoparticles, wherein the nanoparticles are preferentially endocytosed by dendritic cells as compared to macrophages; and applying a variable magnetic field to the subject to generate heat in the cell surrounding the nanoparticles. In one embodiment, the magnetic field is generated by a variable magnetic field generator. In another embodiment, the nanoparticles may be directed to a specific site in the subject using a magnet.

In one aspect, the present invention provides a method of treating a disorder of the immune system comprising administering to a subject having a disorder of the immune system magnetic carbon nanoparticles, wherein the nanoparticles are preferentially endocytosed by dendritic cells as compared to macrophages; and wherein the nanoparticles are conjugated to a cytotoxic agent. In one embodiment, the nanoparticles may be directed to a specific site in the subject using a magnetic field. In particular embodiments, the cytotoxic agent is selected from one or more of the group consisting of: a chemotherapeutic agent, a toxin, or a radioisotope.

In one aspect, the present invention provides a method of diagnosing a disorder of the immune system comprising: administering to a subject having or suspected of having a disorder of the immune system a magnetic carbon nanoparticle, wherein the nanoparticle is preferentially endocytosed by dendritic cells as compared to macrophages; and detecting the presence of the nanoparticle in the subject or a sample isolated from the subject. In one embodiment, the isolated dendritic cells are contacted with T cells of known specificity to test the presence of antigens in patients or the ability of dendritic cells to activate T cells.

In one embodiment, the nanoparticle is conjugated to a fluorescent label, so that detection is accomplished by measuring the fluorescence from the sample isolated from the subject. In another embodiment, detection is accomplished by in vivo magnetic resonance imaging.

BRIEF DESCRIPTION OF THE DRAWINGS

FIG. 3F shows data indicating that an α-DEC 205 antibody increases the efficiency of uptake.

DETAILED DESCRIPTION

Figure 1:
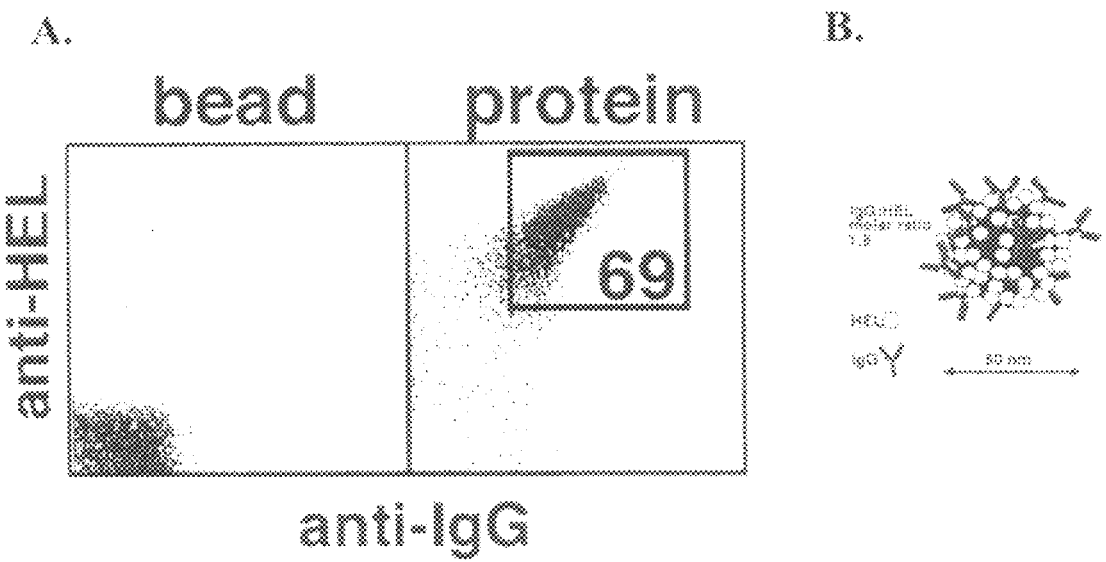
FIG. 1A shows a plot of cytofluorometric analysis of CMNPs before (left panel) and after (right panel) the binding of HELP antigen and anti-DEC 205 antibodies.
FIG. 1B is a schematic representation of the antigen and antibody-coated nanoparticles.

The present invention provides vaccine and diagnostic compositions which target DCs of the immune system. In one aspect, the present invention provides a therapeutic benefit by enhancing the immune response of a subject to various antigens, e.g., infectious disease- or tumor-associated antigens. In another aspect, the present invention provides a therapeutic benefit for the treatment of autoimmune diseases by selectively targeting and killing aberrant DCs. In a third aspect, the present invention provides a means of isolating or monitoring DCs in a subject or a sample.

Definitions

In the description that follows, a number of terms are utilized extensively. Definitions are herein provided to facilitate understanding of the invention. The terms defined below are more fully defined by reference to the specification as a whole. Definitions of other terms may be found in the *Illus-* trated *Dictionary of Immunology*, 2nd Edition (Cruse, J. M. and Lewis, R. E., Eds., Boca Raton, Fla.: CRC Press, 1995).

The terms "a" and "an" as used herein mean "one or more" unless the singular is expressly specified.

As used herein, the "administration" of an agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and administration by another. The various modes of treatment or prevention of medical conditions as described are intended to mean "substantial," which includes total but also less than total treatment or prevention, and wherein some biologically or medically relevant result is achieved.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs are compounds that have the same basic chemical structure as naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as naturally-occurring amino acids. Amino acid mimetics are chemical compounds that have a structure that is different from the general chemical structure of an amino acid, but that functions in a manner similar to a naturally-occurring amino acid. Amino acids can be referred to herein by either their commonly known three-letter symbols or by the one-letter symbols recommended by the IUPAC-IUB Biochemical Nomenclature Commission. Nucleotides, likewise, can be referred to by their commonly accepted single-letter codes.

As used herein, the term "antibody" means a polypeptide comprising a framework region from an immunoglobulin gene or fragments thereof that specifically bind and recognize antigens. Use of the term antibody is meant to include whole antibodies, including single-chain whole antibodies, and antigen-binding fragments thereof. The term "antibody" includes bispecific antibodies and multispecific antibodies so long as they exhibit the desired biological activity or function.

As used herein, the term "antibody-related polypeptide" means antigen-binding antibody fragments, including single-chain antibodies, that can comprise the variable region(s) alone, or in combination with all or part of the following polypeptide elements: hinge region, $CH_1$, $CH_2$, and $CH_3$ domains of an antibody molecule. Also included in the invention are any combination of variable region(s) and hinge region, $CH_1$, $CH_2$, and $CH_3$ domains. Antibody-related molecules useful as binding agents of the invention include, e.g., but are not limited to, Fab, Fab' and $F(ab')_2$, Fd, single-chain Fvs (scFv), single-chain antibodies, disulfide-linked Fvs (sdFv) and fragments comprising either a $V_L$ or $V_H$ domain. Examples include: (i) a Fab fragment, a monovalent fragment consisting of the $V_L$, $V_H$, $C_L$ and $CH_1$ domains; (ii) a $F(ab')_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., *Nature* 341: 544-546, 1989), which consists of a $V_H$ domain; and (vi) an isolated complementarity determining region (CDR). As such, "antibody fragments" can comprise a portion of a full-length antibody, generally the antigen-binding or variable region thereof. Examples of antibody fragments include Fab, Fab', $F(ab')_2$, and Fv fragments; diabodies; linear antibodies; single-chain antibody molecules; and multispecific antibodies formed from antibody fragments. Single-chain antibody molecules may comprise a polymer with a number of individual molecules; for example, dimer, trimer or other polymers.

As used herein, the term "biological sample" means sample material derived from or contacted by living cells. The term "biological sample" is intended to include tissues, cells and biological fluids isolated from a subject, as well as tissues, cells and fluids present within a subject. Biological samples of the invention include, e.g., but are not limited to, whole blood, plasma, semen, saliva, tears, urine, fecal material, sweat, buccal, skin, cerebrospinal fluid, and hair. Biological samples can also be obtained from biopsies of internal organs or from cancers. Biological samples can be obtained from subjects for diagnosis or research, or can be obtained from undiseased individuals as controls or for basic research.

The term "antigen" (Ag) as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. It is readily apparent that an antigen can be generated, synthesized or derived from a biological sample. Such a biological sample can include, but is not limited to, a tissue sample, a tumor sample, a cell or a biological fluid.

"Antigen-presenting cells" (APCs) are cells that are capable of activating T cells, and include, but are not limited to, dendritic cells (DCs), monocytes/macrophages, and B cells. "Antigen-loaded APCs" or an "antigen-pulsed APCs" include APCs that have been exposed to and activated by an antigen. For example, an APC may become Ag-loaded in vitro, e.g., during culture in the presence of an antigen. The APC may also be loaded in vivo by exposure to an antigen. An "antigen-loaded APC" is traditionally prepared in one of two ways: (1) small peptide fragments, known as antigenic peptides, are "pulsed" directly onto the outside of the APCs; or (2) the APC is incubated with whole proteins or protein particles which are then ingested by the APC. These proteins are digested into small peptide fragments by the APC and are eventually transported to and presented on the APC surface. In addition, the antigen-loaded APC can also be generated by introducing a polynucleotide encoding an antigen into the cell.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, and ulcerative colitis, among others.

The term "cancer" as used herein is defined as a disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "dendritic cell" or "DC" refers to any member of a diverse population of morphologically similar cell types found in lymphoid or non-lymphoid tissues. These cells are characterized by their distinctive morphology and high levels of surface MHC-class II expression. DCs can be isolated from a number of tissue sources. DCs have a high capacity for sensitizing MHC-restricted T cells, and are the only antigen-presenting cells (APCs) that can activate naïve T-cells. The antigens may be self-antigens that are expressed during T cell development and tolerance, and foreign antigens that are present during normal immune processes. As used herein, an "activated DC" is a DC that has been pulsed with an antigen and is capable of activating an immune cell. The term "mature DC," as used herein, is defined as a dendritic cell that expresses high levels of MHC class II, CD80 (B7.1) and CD86 (B7.2) molecules. In contrast, immature dendritic cells express low levels of MHC class II, CD80 (B7.1) and CD86 (B7.2) molecules but have a great capacity to take up an antigen.

The term "dense medium" refers to materials that are liquid at the operating conditions in the plasma reactor.

As used herein, the terms "effective amount," "pharmaceutically effective amount" and "therapeutically effective amount" of a composition refer to a quantity sufficient to achieve a desired therapeutic and/or prophylactic effect. In the context of treating a disease or condition, a "therapeutically effective amount" is an amount which results in the prevention of, or a decrease in, the symptoms associated with a disease or condition that is being treated. The amount of a composition of the invention administered to the subject will depend on the type and severity of the disease and on the characteristics of the individual, such as general health, age, sex, body weight and tolerance to drugs. It will also depend on the degree, severity and type of disease. Those of skill in the art will be able to determine appropriate dosages depending on these and other factors. The compositions of the present invention can also be administered in combination with one or more additional therapeutic compounds. In the methods of the present invention, a carbon nanoparticle, optionally conjugated to an antibody and/or a therapeutic agent, is generally administered in an amount wherein uptake by DCs as compared to macrophages is preferred.

As used herein, the term "endocytosis" refers to a process whereby cells absorb material from the outside by engulfing the material with their cell membranes. A type of endocytosis is phagocytosis, which is the process by which cells ingest large objects. The cell membrane folds around the object, and the object is sealed off into a vacuole known as a phagosome.

As used herein, the term "immune response" refers to the concerted action of lymphocytes, antigen-presenting cells, phagocytic cells, granulocytes, and/or soluble macromolecules produced by the above cells or the liver (including antibodies, cytokines, and complement) that results in selective damage to, destruction of, or elimination from the human body of detrimental cells, such as cancerous cells, metastatic tumor cells, malignant melanoma, invading pathogens, cells or tissues infected with pathogens, or, in cases of autoimmunity or pathological inflammation, normal human cells or tissues.

As used herein, "immunogen" refers to a substance that is able to stimulate or induce a humoral antibody and/or cell-mediated immune response in a mammal.

The term "immunoglobulin" or "Ig," as used herein, is defined as a class of proteins that function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most mammals. It is the most efficient immunoglobulin in agglutination, complement fixation, and other antibody responses, and is important in defense against bacteria and viruses. IgD is the surface antigen receptor. IgE is the immunoglobulin that mediates immediate hypersensitivity by causing release of mediators from mast cells and basophils upon exposure to allergens.

As used herein, the term "medical condition" includes, but is not limited to, any condition or disease manifested as one or more physical and/or psychological symptom(s) for which treatment and/or prevention is desirable, and includes previously and newly identified diseases and other disorders. For example, a medical condition may be hepatitis, systemic lupus erythematosus (SLE), cancer, septic shock, stroke, or heart infarction.

The term "major histocompatibility complex," or "MHC," as used herein, is defined as a specific cluster of genes, many of which encode evolutionarily related cell surface proteins involved in antigen presentation, which are among the most important determinants of histocompatibility. Class I MHC, or MHC-I, function mainly in antigen presentation to CD8 T lymphocytes. Class II MHC, or MHC-II, function mainly in antigen presentation to CD4 T lymphocytes.

The term "monoclonal antibody" as used herein refers to an antibody obtained from a population of substantially homogeneous antibodies, i.e., the individual antibodies comprising the population are identical except for possible naturally occurring mutations that may be present in minor amounts. For example, a monoclonal antibody can be an antibody that is derived from a single clone, including any eukaryotic, prokaryotic, or phage clone. The term does not refer to the method by which the antibody is produced. A monoclonal antibody composition displays a single binding specificity and an affinity for a particular epitope. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates that the antibody is obtained from a substantially homogeneous population of antibodies, and is not to be construed as requiring production of the antibody by any particular method. Monoclonal antibodies can be prepared using a wide variety of techniques known in the art including, e.g., but not limited to, hybridoma, recombinant, and phage display technologies. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

As used herein, the term "nanoparticle" refers to particles having nanoscale dimensions. For example, nanoparticles may have a diameter or an average diameter of less than about 100 nm, and preferably less than about 70 nm. In some embodiments of the present invention, the nanoparticles are carbon nanoparticles or carbon magnetic nanoparticles (CMNP). In some embodiments, the nanoparticles are CMNPs and have a diameter from about 30 nm to about 70 nm. As used herein, the term nanoparticle may include spherical nanoparticles as well as non-spherical nanoparticles. For example, the particles may be elongated as in the case of nanowires, nanotubes, and similar structures.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration.

As used herein, the terms "polypeptide," "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

The term "self-antigen" as used herein is defined as an antigen that is expressed by a host cell or tissue. Self-antigens may be tumor antigens, but in certain embodiments are expressed in both normal and tumor cells. A skilled artisan would readily understand that a self-antigen may be overexpressed in a cell.

As used herein, the term "subject" means that preferably the subject is a mammal, preferably a human, but can also be an animal such as a domestic animal (e.g., dogs, cats and the like), farm animal (e.g., cows, sheep, pigs, horses and the like) or laboratory animal (e.g., monkey, rats, mice, rabbits, guinea pigs and the like).

As used herein, the term "therapeutic agent" is intended to mean a compound that, when present in an effective amount, produces a desired therapeutic effect on a subject in need thereof.

As used herein, the terms "treating," "treatment" and "alleviation" refer to both therapeutic treatment and prophylactic or preventative measures, wherein the object is to prevent or slow down (lessen) the targeted pathologic condition or disorder. A subject is successfully "treated" for a disorder if the subject shows observable and/or measurable reduction in or absence of one or more signs and symptoms of a particular disease or condition. For example, for cancer, successful treatment is indicated by a reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, of one or more of the symptoms associated with the specific cancer; reduced morbidity and mortality; and improvement in quality of life issues.

The terms "transfected," "transformed" and "transduced," as used herein, refer to a process by which exogenous nucleic acid is transferred or introduced into the host cell. A "transfected," "transformed" or "transduced" cell is one which has been transfected, transformed or transduced with exogenous nucleic acid. The cell includes the primary subject cell and its progeny.

As used herein, the term "tumor-associated antigen" refers to antigens that are common to specific hyperproliferative disorders. In certain aspects, the tumor-associated antigens of the present invention are derived from cancers including, but not limited to, primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

The term "vaccine" as used herein is defined as a material used to provoke an immune response after administration of the material to a mammal.

Compositions of the Invention
  General.

In one aspect, the present invention provides carbon nanoparticles that are preferentially endocytosed by DCs as compared to macrophages. In one embodiment, the nanoparticles are carbon cage nanoparticles, such as fullerenes. In some embodiments, these nanoparticles are magnetic carbon nanoparticles (CMNP). The nanoparticles may further be conjugated to one or more additional compounds, including, but not limited to, targeting compounds (e.g., antibodies and receptor ligands), therapeutic agents, or detectable labels.

The nanoparticles of the present invention are preferentially endocytosed by DCs as compared to macrophages. By "preferentially" it is meant that the nanoparticles may be largely or essentially endocytosed by DCs, although some endocytosis by other cells (e.g., macrophages) may be tolerated or even desired for some purposes. Generally, though, endocytosis will be at least 50% greater, at least 100% greater, or at least 200% greater in DCs compared to other cells. While not wishing to be limited by theory, it is believed that nanoparticles having the approximate size of a virus are taken up by DCs as compared to macrophages. Consequently, in some embodiments, the compositions of the present invention may comprise nanoparticles having a diameter or average diameter from about 30 nm to about 70 nm. In some embodiments, the compositions predominantly comprise nanoparticles having an average diameter from about 50 nm to 70 nm, or from about 55 nm to 65 nm, or from about 58 nm to 62 nm.

Targeting Moieties.

The nanoparticles of the present invention may be conjugated with targeting moieties to enhance the uptake of the nanoparticle by DCs. In one embodiment, the nanoparticles are conjugated to antibodies which specifically bind to molecules on the surface of DCs. Antigens present on the surface of DCs include, but are not limited to, DEC-205, DC-SIGN, and mannose receptor (MR), Fc receptors, and CD40. For example, an anti-DEC-205 antibody may be conjugated to carbon nanoparticles in order to augment the uptake of the nanoparticle by DCs. In another embodiment, nanoparticles may be conjugated to receptor ligands, wherein the corresponding receptor is expressed on the surface of the DCs. For example, a DC receptor may include, but is not limited to, ICAM-2 and PDI.

Vaccine Compositions
  General.

The present invention includes vaccine compositions for "pulsing" APCs (e.g., DCs) with an antigen, thereby activating the DC to stimulate an immune response. For example, an APC may be pulsed in vitro, e.g., by culture ex vivo in the presence of a nanoparticle conjugated to an antigen, or in vivo by exposure to a nanoparticle conjugated to an antigen. An APC can be "pulsed" in a manner that exposes the APC to an antigen for a time sufficient to promote presentation of that antigen on the surface of the APC. For example, an APC can be exposed to an antigen in a form of small peptide fragments, known as antigenic peptides; or APCs can be incubated with whole proteins or protein particles which are then ingested by the APCs. These whole proteins are digested into small peptide fragments by the APC and eventually carried to and presented on the APC surface. Antigen in peptide form may be exposed to the cell by "pulsing" techniques described herein. In one embodiment, carbon nanoparticles are used to facilitate the uptake of antigens by APCs.

Without wishing to be bound by theory, it is believed that the antigen in the form of a foreign or an autoantigen may be processed by an APC in order to retain the immunogenic form of the antigen. The immunogenic form of the antigen implies processing of the antigen through fragmentation to produce a form of the antigen that can be recognized by and stimulate immune cells, for example T cells. Preferably, such a foreign or an autoantigen is a protein which is processed into a peptide by the APC. The relevant peptide which is produced by the APC may be extracted and purified for use as an immunogenic composition. Peptides processed by the APC may also be used to induce tolerance to the proteins processed by the APC.

It is believed that autoimmune diseases result from an immune response being directed against "self-proteins," otherwise known as autoantigens, i.e., autoantigens that are present or endogenous in an individual. In an autoimmune response, these "self-proteins" are presented to T cells, which causes the T cells to become "self-reactive." According to the method of the invention, APCs are pulsed with an antigen to produce the relevant "self-peptide." The relevant self-peptide is different for each individual because MHC products are highly polymorphic and each individual MHC molecule might bind different peptide fragments. The "self-peptide" and an agonist of inhibitors of cytokine signaling can then be used to design competing peptides or to induce tolerance to the self protein in the individual in need of treatment.

The antigen-activated APC, otherwise known as a "pulsed APC," is produced by exposure of the APC to an antigen either in vitro or in vivo. In the case where the APC is pulsed in vitro, the APC is plated on a culture dish and exposed to a nanoparticle conjugated to the antigen in a sufficient amount and for a sufficient period of time to allow the antigen to bind to the APC. The amount and time necessary to achieve binding of the antigen to the APC may be determined by using methods known in the art or otherwise disclosed herein. Other methods known to those of skill in the art (for example immunoassays or binding assays) may be used to detect the presence of antigen on the APC following exposure to the antigen.

In a further embodiment of the invention, the APC may be transfected with a vector which allows for the expression of a specific protein by the APC. The protein which is expressed by the APC may then be processed and presented on the cell surface on an MHC receptor. The transfected APC may then be used as an immunogenic composition to produce an immune response to the protein encoded by the vector. Transfection of DCs may be accomplished by conjugating a polynucleotide vector to carbon nanoparticles, which are preferentially endocytosed by DCs as compared to macrophages.

A polynucleotide encoding an antigen can be cloned into an expression vector and the vector can be introduced into an APC to generate an activated APC. For example, a vector encoding an antigen may be introduced into a host cell by any method in the art. For example, the expression vector can be prepared using standard procedures. See, for example, Sambrook et al. (2001, *Molecular Cloning: A Laboratory Manual*, Cold Spring Harbor Laboratory, New York), and in Ausubel et al. (1997, *Current Protocols in Molecular Biology*, John Wiley & Sons, New York). It is readily understood that the introduction of the expression vector comprising a polynucleotide encoding an antigen yields a pulsed cell.

The present invention includes various methods for pulsing APCs using carbon nanoparticles including, but not limited to, loading APCs with whole antigen in the form of a protein, cDNA or mRNA. However, the invention should not be construed to be limited to the specific form of the antigen used for pulsing the APC. Rather, the invention encompasses other methods known in the art for generating an antigen-loaded APC. For example, the APC is transfected with mRNA, encoding a defined antigen corresponding to a gene product whose sequence is known can be rapidly generated in vitro using appropriate primers and reverse transcriptase-polymerase chain reaction (RT-PCR) coupled with transcription reactions. The RNA may then be conjugated to a carbon nanoparticle. Transfection of an APC with an mRNA provides an advantage over other antigen-loading techniques for generating a pulsed APC. For example, the ability to amplify RNA from a microscopic amount of tissue, i.e., tumor tissue, extends the use of the APC for vaccination to a large number of patients.

Antigens useful in the vaccine compositions of the present invention may come from a variety of sources. The antigen may be derived from a virus, a fungus, or a bacterium. The antigen may be a self-antigen or an antigen associated with a disease selected from the group consisting of an infectious disease, a cancer, or an autoimmune disease.

For an antigenic composition to be useful as a vaccine, the antigenic composition must induce an immune response to the antigen in a cell, tissue or mammal (e.g., a human). As used herein, an "immunological composition" may comprise an antigen (e.g., a peptide or polypeptide), a nucleic acid encoding an antigen (e.g., an antigen expression vector), or a cell expressing or presenting an antigen or cellular component. In particular embodiments, the antigenic composition comprises or encodes all or part of any antigen described herein, or an immunologically functional equivalent thereof. In other embodiments, the antigenic composition is in a mixture that comprises an additional immunostimulatory agent or nucleic acids encoding such an agent. Immunostimulatory agents include but are not limited to an additional antigen, an immunomodulator, an antigen-presenting cell or an adjuvant. In other embodiments, one or more of the additional agent(s) is covalently bonded to the antigen or an immunostimulatory agent, in any combination. In certain embodiments, the antigenic composition is conjugated to or comprises HLA anchor motif amino acids.

It is understood that an antigenic composition of the present invention may be made by a method that is well known in the field, including but not limited to chemical synthesis by solid-phase synthesis and purification away from the other products of the chemical reactions by HPLC, or production by the expression of a nucleic acid sequence (e.g., a DNA sequence) encoding a peptide or polypeptide comprising an antigen of the present invention in an in vitro translation system or in a living cell. In addition, an antigenic composition can comprise a cellular component isolated from a biological sample. Preferably, the antigenic composition is isolated and extensively dialyzed to remove one or more undesired small molecular weight molecules and/or lyophilized for more ready formulation into a desired vehicle. It is further understood that additional amino acids, mutations, chemical modification and the like, if any, that are made in a vaccine component will preferably not interfere substantially with the antibody recognition of the epitopic sequence.

A peptide or polypeptide corresponding to one or more antigenic determinants of the present invention should generally be at least five or six amino acid residues in length, and may contain up to about 10, about 15, about 20, about 25, about 30, about 35, about 40, about 45 or about 50 residues. A peptide sequence may be synthesized by methods known to those of ordinary skill in the art, such as, for example, peptide synthesis using automated peptide synthesis machines, such as those available from Applied Biosystems, Inc. (Foster City, Calif.). Longer peptides or polypeptides also may be prepared, e.g., by recombinant means.

In certain embodiments, a nucleic acid encoding an antigenic composition and/or a component described herein may be used, for example, to produce an antigenic composition in vitro or in vivo for the various compositions and methods of the present invention. For example, in certain embodiments, a nucleic acid encoding an antigen is carried by a vector in a recombinant cell. The nucleic acid may be expressed to produce a peptide or polypeptide comprising an antigenic sequence. The peptide or polypeptide may be secreted from the cell, or may be part of or within the cell. DNA coupled to CMNP can be detected by PCR to trace the presence of minute amounts of CMNP in ex vivo samples.

Tumor Associated Antigens.

In one embodiment, a tumor antigen of the present invention comprises one or more antigenic cancer epitopes immunologically recognized by tumor-infiltrating lymphocytes (TIL) derived from a cancer tumor of a mammal. Malignant tumors express a number of proteins that can serve as target antigens for an immune attack. These molecules include, but are not limited to, tissue-specific antigens such as MART-1, tyrosinase and GP 100 in melanoma; and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are oncofetal antigens such as carcinoembryonic antigen (CEA). In B-cell lymphoma, the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have also been used as targets for passive immunotherapy with monoclonal antibodies.

Microbial Antigens.

Microbial antigens may be viral, bacterial, or fungal in origin. Examples of infectious viruses include: Retroviridae (e.g., human immunodeficiency viruses, such as HIV-1 (also referred to as HTLV-III, LAV or -HTLV-III/LAV, or HIV-III); and other isolates, such as HIV-LP); Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses.

Examples of infectious bacteria include: *Helicobacter pyloris, Borelia burgdorferi, Legionella pneumophilia, Mycobacteria* sps (e.g., *M. tuberculosis, M. avium, M. intracellulare, M. kansasii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema Treponema pertenue, Leptospira,* and *Actinomyces israelli.*

Examples of infectious fungi include: *Cryptococcus neoformans, Histoplasma capsulatum, Coccidioides immitis, Blastomyces dermatitidis, Chlamydia trachomatis, Candida albicans.* Other infectious organisms (i.e., protists) including: *Plasmodium falciparum* and *Toxoplasma gondii.*

Diagnostic Compositions.

In one embodiment, the nanoparticle compositions of the present invention are coupled with a label moiety, i.e., a detectable group. The particular label or detectable group conjugated to the nanoparticle compositions of the invention is not a critical aspect of the invention, so long as it does not significantly interfere with the endocytosis of the nanoparticles by DCs. The detectable group can be any material having a detectable physical or chemical property. Such detectable labels have been well-developed in the field of immunoassays and imaging. In general, nearly any label useful in such methods can be applied to the present invention. Thus, a label is any composition detectable by spectroscopic, photochemical, biochemical, immunochemical, electrical, optical or chemical means. Useful labels in the present invention include fluorescent dyes (e.g., fluorescein isothiocyanate, Alexa dyes, Texas red, rhodamine, and the like), radiolabels (e.g., $^{3}$H, $^{14}$C, $^{35}$S, $^{125}$I, $^{121}$I, $^{131}$I, $^{112}$In, $^{99}$mTc), $^{18}$F, $^{11}$C, $^{15}$O, (for Positron emission tomography), $^{99}$mTC, $^{111}$In (for single-photon emission tomography), and calorimetric labels such as colloidal gold or colored glass or plastic (e.g., polystyrene, polypropylene, latex, and the like) beads. Patents that described the use of such labels include U.S. Pat. Nos. 3,817, 837; 3,850,752; 3,939,350; 3,996,345; 4,277,437; 4,275,149; and 4,366,241, each of which is incorporated herein by reference in its entirety and for all purposes. See also *Handbook of Fluorescent Probes and Research Chemicals* (6th Ed., Molecular Probes, Inc., Eugene Oreg.).

The label can be coupled directly or indirectly to the desired component of an assay according to methods well known in the field. As indicated above, a wide variety of labels can be used, with the choice of label depending on the sensitivity required, ease of conjugation with the compound, stability requirements, available instrumentation, and disposal provisions. In one embodiment, the label is coupled indirectly via a biotinylated probe bound to avidin which is coupled to the CMNP.

Therapeutic Compositions

In one aspect, the carbon nanoparticles of the present invention are conjugated to a cytotoxic agent such as a chemotherapeutic agent, a toxin (e.g., an enzymatically active toxin of bacterial, fungal, plant, or animal origin, or fragments thereof), or a radioactive isotope (i.e., a radioconjugate). Such compositions are useful, for example, in treating subjects having autoimmune diseases with aberrant DC activity. Elimination of DC by toxins may ease autoimmune diseases such as multiple sclerosis, rheumatoid arthritis, autoimmune diseases, and others.

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the carbon nanoparticles and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the carbon nanoparticles.

Synthesis of Carbon Nanoparticles of the Present Invention

The nanoparticles may be formed using a variety of techniques known in the art. In one embodiment, the carbon nanoparticles of the present invention are carbon magnetic nanoparticles (CMNP) which may be synthesized, for example, in a dense medium plasma according to U.S. Pat. No. 7,128,816. In one embodiment, the carbon nanoparticles of the present invention are about 99% to 99.5% carbon and about 0.5% to 1% iron oxide. Briefly, the plasma synthesis of CMNP from benzene may be performed using a Dense Medium Plasma reactor provided with iron electrodes, which allows the initiation and sustaining of discharges at atmospheric pressure environments in co-existing liquid/vapor media, which may offer significantly higher efficiency for the processing of liquid-phase materials in comparison to other plasma technologies.

Iron- and silver-containing, carbon-based nanoparticles may be synthesized using the patented Dense Medium Plasma (DMP) approach, which is an atmospheric pressure, submerged arc technique (U.S. Pat. No. 7,128,816). Both rotating-electrode and cylindrical electron configuration plasma tools may be used in the synthesis of nanoparticles. Depending on the nature of the electron materials employed, iron, silver, or combined iron and silver nanoparticles may be incorporated into the nascent carbon-cage nanostructures. The resulting nanoparticles have a narrow size distribution and high surface area, and are thermally stable. Depending on the chemical nature of the starting liquid-phase material, such as benzene, indene, acetonitrile, pyrazine, etc., carbon or carbon and nitrogen may be incorporated into the structure of the nanoparticles. The presence of unsaturated bonds and the primary, secondary and tertiary amine functionalities in the structure of the nanobeads as a result of the discharged-induced dehydrogenation and rehydrogenation reaction mechanisms make these nanoparticles extremely attractive for further "ex situ" functionalization reaction. The presence of these functionalities allows a covalent attachment of active low- and high-molecular weight, active biomolecules to the nanoparticles. Incorporation at the same time of electrode-origin silver nanoparticles into the bead structures produces strong antimicrobial behavior with great potential for targeted bioengineering. Iron-containing carbon nanoparticles, and especially those synthesized from benzene and indene using the cylindrical electrode-configuration plasma reactor, contain significantly higher iron concentration (>5%). This higher iron concentration opens up an efficient way to remote access these particles using an alternative magnetic field for the generation of hyperthermal effects in targeted cells.

In one embodiment, a nanoparticle having primary amine functionalities may be conjugated to a biomolecule, e.g., a protein, peptide, or nucleic acid. In a slightly alkaline environment, aldehydes and ketones can react with primary and secondary amino groups to form Schiff bases. This reaction may be used by many for coupling ligands, spacers, or proteins to certain supports. In one embodiment, glutaraldehyde-mediated covalent coupling is used to introduce amine functionalities to the nanoparticles (See Example 2).

In another embodiment, a vacuum condensation reaction is used to introduce amine functionalities to the nanoparticles. Condensation reactions including step polymerization processes are equilibrium reactions, and proper means must be employed to displace the equilibrium in the direction of the condensation product. Removal of small molecular weight byproducts of the process must be carried out in this purpose. Some of the condensation reactions such as the formation of amide groups (e.g., polyamides), proceed at reasonable rates even as uncatalyzed mechanisms. In most cases, these condensation reactions must be carried out in an open, driven system. That is, at least one of the products of the forward reactions must be removed to drive the equilibrium toward condensation. It is usually more convenient to remove the small-molecular weight byproduct. When water is the byproduct (e.g., in reactions that involve biomolecules) it can be removed by a combination of temperature adjustment and reduced pressure (e.g., vacuum-driven evaporation). However, driving the equilibrium in conventional polycondensation reactions is not an easy task. The resulting small molecules that diffuse in the reaction mixture should diffuse out through a viscous environment. In solid-state condensation reactions, including the solid-phase synthesis of peptides, and condensation reactions that proceed in the interphase structure of surface layers such as surface-functionalized nanoparticles, this process can be carried out much more easily when the reaction is controlled by the rate of removal of the small-molecular weight compounds, rather than by diffusion. It also should be assumed that at elevated vacuum conditions, molecular reorientation (e.g., formation of ordered molecular assemblies) and formation of hydrogen bonding will be enhanced. This processes could lower the activation energy of the condensation reactions (covalent bond-formation process). This low pressure-evaporation condensation has been used to covalently attach biomolecules onto nanoparticle surfaces.

Uses of the Compositions of the Present Invention
  General.

The present invention provides for diagnostic, prophylactic, and therapeutic methods of treating a subject at risk of (or susceptible to) developing a disorder, or having a disorder, associated with altered immune system function. In one embodiment, the compositions of the invention are useful in methods to isolate DCs. A nanoparticle preferentially endocytosed by DCs as compared to macrophages can facilitate the purification of DCs from biological samples, e.g., mammalian sera or tissues. In another embodiment, the nanoparticle compositions of the invention can be used diagnostically to monitor DCs in a subject or particular tissue as part of a clinical testing procedure, e.g., to determine the efficacy of a given treatment regimen. As noted above, the detection can be facilitated by coupling (i.e., physically linking) the nanoparticle of the invention to a detectable substance or by detecting magnetic nanoparticles using magnetic resonance imaging. In another embodiment, the compositions can be used as vaccine delivery systems in order to target antigens to antigen-presenting cells. In another embodiment, a therapeutically effective amount of nanoparticle compositions, optionally conjugated to one or more therapeutic agents, is administered so as to provide therapeutic benefits against the secondary effects from aberrant DC activity, i.e., autoimmune activity. In one embodiment, the nanoparticle is a CMNP, which may be heated using a variable magnetic field generator, thereby destroying the surrounding cell. Optionally, the administration is made during the course of adjunct therapy, such as combined cycles of radiation, chemotherapeutic treatment, or administration of any other cytoprotective or immunomodulatory agent. As such, the nanoparticle compositions of the present invention and a compound useful in adjunct therapy may be administrated simultaneously and sequentially to a subject.

Purification of DCs

In one aspect, the compositions of the present invention may be used to enrich DCs from the circulating blood of patients, e.g., cancer patients. The DCs may then be pulsed with an antigen and reintroduced into the patient. These dendritic cell therapies (DCT) are designed to enhance or inhibit immunity.

In one embodiment, DCs are purified from a culture of cells. The procedure for ex vivo expansion of hematopoietic stem and progenitor cells described in U.S. Pat. No. 5,199,942 can be applied to cells of the present invention. Other suitable methods are known in the art, therefore, the present invention is not limited to any particular method of ex vivo expansion of the cells. Briefly, ex vivo culture and expansion of DCs comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors, such as flt3-L, IL-1, IL-3 and c-kit ligand, can be used for culturing and expanding the cells.

A variety of cell selection techniques are known for identifying and separating CD34+ hematopoietic stem or progenitor cells from a population of cells. For example, monoclonal antibodies (or other specific cell binding proteins) can be used to bind to a marker protein or surface antigen protein found on stem or progenitor cells. Several such markers or cell surface antigens for hematopoietic stem cells (i.e., flt-3, CD34, My-10, and Thy-1) are known in the art.

The collected CD34+ cells are cultured with suitable cytokines. CD34+ cells are then allowed to differentiate and commit to cells of the dendritic lineage. These cells may be further purified using the CMNP of the present invention. The enriched sample of DCs may then be pulsed with an antigen and infused into a subject. After the cells are infused, some will migrate to the lymph nodes and some will stay in the circulation. The likelihood is high that many of the DCs will come in contact with T-lymphocytes (CTL) and stimulate them to divide, and recognize and kill tumor cells.

Cells may also be purified by flow cytometry, using markers characteristic of DCs, such as CD1a, HLA DR, CD80 and/or CD86. Following isolation and culturing of DCs, the cells can be modified according to the methods of the present invention. Alternatively, the progenitor cells can be modified prior to being differentiated to DC-like cells.

Diagnostic Uses of Nanoparticle Compositions of the Invention

In one aspect, the present invention provides diagnostic methods for determining the quantity or type of DCs in a sample, or the localization of DCs within a subject. DCs are highly efficient APCs and are largely considered to be the only cell type responsible for the initiation of primary immune responses through activation of naïve T cells. DCs can also induce immune tolerance. DCs can be characterized according to their maturation status, ability to migrate, ability to capture and present antigens to naïve T cells, and ability to induce either a productive immune response or self-tolerance. With regard to maturation status, DCs can be broadly classified as either immature or mature, based primarily upon functional phenotype. Immature DCs can very efficiently capture antigens for subsequent processing and presentation to naïve T cells. In the absence of infectious or inflammatory signals, immature DCs most likely remain undifferentiated and undergo deletion, anergy, or differentiation into regulatory T cells. Conversely, in the presence of infectious or inflammatory signals, immature DCs undergo maturation, up-regulate MHC and co-stimulatory (e.g., CD40, CD80, CD86) molecules, migrate to secondary lymphoid organs, and induce specific immune responses. Depending on the maturation signal and immune environment, mature DCs can induce pro-inflammatory TH1 or TH2 CD4+ T cell differentiation, and/or activate cytotoxic CD8+ T cells. In addition to functional phenotype, DCs are often characterized according to cell surface marker expression, including MHC class II, CD11b, CD11c, CD80, CD40, B220 and CD8α.

In one embodiment, enriched DCs can be tested for different properties that are useful in the diagnosis and treatment of diseases. Using co-stimulatory, molecule-specific antibodies, the activation stages of DCs can be determined. For example, a high level of co-stimulation is a marker of inflammation and an immunostimulatory environment. Further, a patient's blood can be tested to see if DCs can activate the patients T cells. A patient having antigen-primed T cells can be tested for DCs to determine if they are capable of restimulating these cells. Such restimulation could indicate that activated DCs present specific antigens. That information can help to identify infection, determine the effectiveness of vaccines, or identify autoimmune processes.

The term "labeled," with regard to the nanoparticle composition, is intended to encompass direct labeling of the binding agent by coupling (i.e., physically linking) a detectable substance to the binding agent, as well as indirect labeling of the binding agent by reactivity with another compound that is directly labeled. Examples of indirect labeling include detection of a primary antibody using a fluorescently-labeled secondary antibody and end-labeling of a DNA probe with biotin such that it can be detected with fluorescently-labeled streptavidin. In some embodiments where the nanoparticle is magnetic, the composition may be detected using, e.g., MRI. Such a technique could be helpful to monitor the effectiveness of DC therapies.

Vaccine Delivery System

General.

This invention provides methods of inducing an immune response in a subject, comprising administering to the subject an effective amount of one or more of the nanoparticle compositions described above under the conditions necessary to induce an immune response to a polypeptide. In such methods, the nanoparticle is conjugated to at least one antigen, which may be a polypeptide or a nucleic acid encoding a polypeptide. The nanoparticle compositions may be combined with a pharmaceutically acceptable carrier. The methods of this invention can be further modified by co-administering an effective amount of an adjuvant, cytokine or co-stimulatory molecule to the subject.

The vaccine compositions may be administered to the subject directly, or, in the alternative, administered to isolated APCs, such as DCs, which are introduced to the patient. DCs may be isolated from a patient by either: (1) isolating bone marrow precursor cells (CD34$^+$) from blood and stimulating them to differentiate into APCs; or (2) collecting the precommitted APCs from peripheral blood. In the first approach, the patient must be treated with cytokines such as GM-CSF to boost the number of circulating CD34$^+$ stem cells in the peripheral blood.

The second approach for isolating APCs is to collect the relatively large numbers of precommitted APCs already circulating in the blood. Previous techniques for isolating committed APCs from human peripheral blood have involved combinations of physical procedures such as metrizamide gradients and adherence/nonadherence steps (Freudenthal, P. S. et al. (1990) *PNAS* 87: 7698-7702); Percoll gradient separations (Mehta-Damani, et al. (1994) *J. Immunol.* 153: 996-1003); and fluorescence-activated cell-sorting techniques (Thomas, R. et al. (1993) *J. Immunol.* 151:6840-52).

One technique for separating large numbers of cells from one another is known as countercurrent centrifugal elutriation (CCE). In this technique, cells are subject to simultaneous centrifugation and a washout stream of buffer which is constantly increasing in flow rate. The constantly increasing countercurrent flow of buffer leads to fractional cell separations that are largely based on cell size.

In one embodiment, the APCs are precommitted or mature DCs which can be isolated from the white blood cell fraction of a mammal, such as a murine, simian or a human (See, e.g., WO 96/23060). The white blood cell fraction can be taken from the peripheral blood of the mammal. This method includes the following steps: (a) providing a white blood cell fraction obtained from a mammalian source by methods known in the art such as leukophoresis; (b) separating the white blood cell fraction of step (a) into four or more subfractions by countercurrent centrifugal elutriation; (c) stimulating conversion of monocytes in one or more fractions from step (b) to dendritic cells by contacting the cells with calcium ionophore, GM-CSF and IL-13 or GM-CSF and IL-4; (d) identifying the dendritic cell-enriched fraction from step (c), and (e) collecting the enriched fraction of step (d), preferably at about 4° C. One way to identify the dendritic cell-enriched fraction is by fluorescence-activated cell sorting. The white blood cell fraction can be treated with calcium ionophore in the presence of other cytokines, such as recombinant (rh) rhIL-12, rhGM-CSF, or rhIL-4. The cells of the white blood cell fraction can be washed in buffer and suspended in Ca$^{++}$/Mg$^{++}$ free media prior to the separating step. The white blood cell fraction can be obtained by leukapheresis. The dendritic cells can be identified by the presence of at least one of the following markers: HLA-DR, HLA-DQ, or B7.2, and the simultaneous absence of the following markers: CD3, CD14, CD16, 56, 57, and CD 19, 20. Monoclonal antibodies specific to these cell surface markers are commercially available.

More specifically, the method requires collecting an enriched collection of white cells and platelets from leukapheresis that is then further fractionated by countercurrent centrifugal elutriation (CCE) (Abrahamsen, T. G. et al. (1991) *J. Clin. Apheresis*. 6:48-53). Cell samples are placed in a special elutriation rotor. The rotor is then spun at a constant speed of, for example, 3000 rpm. Once the rotor has reached the desired speed, pressurized air is used to control the flow rate of cells. Cells in the elutriator are subjected to simultaneous centrifugation and a washout stream of buffer which is constantly increasing in flow rate. This results in fractional cell separations based largely but not exclusively on differences in cell size.

The purified or partially purified DC fractions may then be used with the nanoparticle compositions described herein. In one embodiment, the nanoparticle compositions are conjugated to an antigen which is taken up by the DCs. "Pulsed" DCs may then be administered to a patient. In a specific embodiment, the antigen is a tumor-associated antigen and the pulsed DCs are administered to a subject having or suspected of having a cancer correlated with the tumor-associated antigen.

Dosage.

Each application requires different doses that can be established by previous titration. For immunization, the antigen content on the CNPs can be used as a measure for dosing. For example, about $\frac{1}{10}^{th}$ to $\frac{1}{100}^{th}$ of the antigen protein on CNPs induces responses similar to the isolated protein not conjugated to a CNP. In in vitro experiments, the magnetic enrichment of dendritic cell recovery can be detected as a function of nanobead concentration. Generally, about 0.1% nanobead solution is sufficient for the treatment of $10^5$ cells or for the recovery of $10^6$ cells. In other embodiments, a nanobead solution of about 0.2%, 0.5%, 1%, 2%, or 5%, or more is used in a treatment regimen.

In other embodiments, the nanoparticle compositions may be administered in dosage ranges from about 0.0001 to 100 mg/kg, and more usually 0.01 to 5 mg/kg of the host body weight every week, every two weeks or every three weeks. For example dosages can be 1 mg/kg body weight or 10 mg/kg body weight every week, every two weeks or every three weeks or within the range of 1-10 mg/kg every week, every two weeks or every three weeks. In one embodiment, a single dosage of nanoparticle compositions ranges from 0.1-10,000 micrograms per kg body weight.

In one embodiment, nanoparticle concentrations in a carrier range from 0.2 to 2000 micrograms per delivered milliliter. An exemplary treatment regime entails administration once every two weeks or once a month or once every 3 to 6 months. Nanoparticle compositions are usually administered on multiple occasions. Intervals between single dosages can be daily, weekly, monthly or yearly. Intervals can also be irregular, as indicated by measuring blood levels of antibody in the subject. Alternatively, nanoparticle compositions can be administered as a sustained release formulation, in which case less frequent administration is required. Dosage and frequency vary depending on the half-life of the nanoparticle compositions in the subject. The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of the symptoms of the disease. Thereafter, the patent can be administered a prophylactic regime.

Toxicity.

Preferably, an effective amount (e.g., dose) of the nanoparticle compositions described herein will provide therapeutic benefit without causing substantial toxicity to the subject. Toxicity of the nanoparticle compositions described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in humans. The dosage can vary within this range depending upon the dosage form employed and the route of administration utilized. The exact formulation, route of administration, and dosage can be chosen by the individual physician in view of the subject's condition. See, e.g., Fingl et al., In: *The Pharmacological Basis of Therapeutics*, Ch. 1 (1975).

Formulations of Pharmaceutical Compositions.

According to the methods of the present invention, the nanoparticle compositions can be incorporated into pharmaceutical compositions suitable for administration. The pharmaceutical compositions generally comprise nanoparticles conjugated to one or more therapeutic agents and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (see, e.g., *Remington's Pharmaceutical Sciences*, Mack Publishing Co., Easton, Pa. 18$^{th}$ ed., 1990). The pharmaceutical compositions are generally formulated to be sterile, substantially isotonic, and in full compliance with all Good Manufacturing Practice (GMP) regulations of the U.S. Food and Drug Administration.

The terms "pharmaceutically-acceptable" and "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of aerosol compositions, gaseous.

Examples of carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the nanoparticle compositions, use thereof in the compositions is contemplated. Supplementary active compounds can also be incorporated into the compositions.

A pharmaceutical composition of the invention is formulated to be compatible with its intended route of administration. The nanoparticle compositions of the present invention can be administered by parenteral, topical, intravenous, oral, subcutaneous, intra-arterial, intradermal, transdermal, rectal, intracranial, intraperitoneal, intranasal, or intramuscular routes, or as inhalants. The nanoparticle compositions can be optionally administered in combination with other agents that are at least partly effective in treating various diseases including various DC-related diseases.

Solutions or suspensions used for parenteral, intradermal, intranasal, or subcutaneous application can include the following components: a sterile diluent for injection such as water, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes, or multiple-dose vials made of glass or plastic.

Pharmaceutical compositions suitable for injectable use include sterile aqueous solutions (where the composition is water soluble) or dispersions and sterile powders for the extemporaneous preparation of sterile injectable solutions or inhaling or dispersion. For intravenous administration, suitable carriers include physiological saline, bacteriostatic water, Cremophor ELTM (BASF, Parsippany, N.J.), or phosphate-buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion, and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol and sorbitol, or sodium chloride, in the composition.

Sterile, injectable solutions can be prepared by incorporating the nanoparticle compositions in the required amount in an appropriate solvent with one or a combination of ingredients enumerated above, as required, followed by filtered sterilization. Generally, dispersions are prepared by incorporating the binding agent into a sterile vehicle that contains a basic dispersion medium and the required other ingredients from those enumerated above. In the case of sterile powders for the preparation of sterile injectable solutions, methods of preparation include vacuum-drying and freeze-drying to yield a powder of the active ingredient, plus any additional desired ingredient, from a previously sterile-filtered solution thereof. The agents of this invention can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the binding agent can be incorporated with excipients and used in the form of a tablet, troche, or capsule. Oral compositions can also be prepared using a fluid carrier for use as a mouthwash, wherein the compound in the fluid carrier is applied orally and swished and expectorated or swallowed. Pharmaceutically compatible binding compounds and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the nanoparticle compositions are delivered in the form of an aerosol spray from a pressured container or dispenser which contains a suitable propellant (e.g., a gas such as carbon dioxide), or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the nanoparticle compositions are formulated into ointments, salves, gels, or creams as generally known in the art.

Detection of Dendritic Cells

An exemplary method for detecting the presence or absence of DCs in a biological sample involves obtaining a biological sample from a test subject and contacting the biological sample with a nanoparticle composition of the invention capable of being preferentially endocytosed by DCs as compared to macrophages in the biological sample. If the nanoparticle is conjugated to a detectable moiety (e.g., a fluorescent label or radioisotope), the moiety can be observed using an appropriate instrument.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, or by the use of electronic detectors such as charge coupled devices (CCDs) or photomultipliers and the like. Similarly, enzymatic labels can be detected by providing the appropriate substrates for the enzyme and detecting the resulting reaction product. Finally simple colorimetric labels can be detected simply by observing the color associated with the label. Thus, in various dipstick assays, conjugated gold often appears pink, while various conjugated beads appear to be the color of the bead.

In another embodiment, the nanoparticle compositions may be administered to a subject under conditions in which the nanoparticle compositions are preferentially endocytosed by DCs as compared to macrophages. The nanoparticle compositions may the be detected in situ, using e.g., MRI. Alternatively, a biological sample may be obtained and the presence or absence of a DC in the biological sample may be observed.

Preferentially Heating/Destroying DCs

The present invention provides methods of preferentially destroying DCs, such as those DCs having aberrant activity, as in autoimmune diseases. In one embodiment, CMNPs which are preferentially endocytosed by DCs as compared to macrophages are administered to a subject. After a period of time, during which the DCs are taken up by the cells, a variable magnetic field may be applied to the subject, which causes heating of the CMNPs. Consequently, the cells and the tissues surrounding cells are killed by the heat. Similarly, toxin-coupled CMNPs can be used for preferential elimination of DCs. The efficiency of DC depletion can be detected by cytofluorimetry by measuring the decrease of cells that express DC markers or by biopsy and immune histochemistry of a section.

All publications, patent applications, issued patents, and other documents referred to in the present disclosure are herein incorporated by reference as if each individual publication, patent application, issued patent, or other document were specifically and individually indicated to be incorporated by reference in its entirety. Definitions that are contained in text incorporated by reference are excluded to the extent that they contradict definitions in this disclosure.

EXAMPLES

The present invention is further illustrated by the following examples, which should not be construed as limiting in any way.

Example 1

Preparation of Carbon Nanoparticles

The plasma synthesis of CMNP from benzene may be performed using a dense medium plasma reactor (DMP), as described in U.S. Pat. No. 7,128,816. The DMP reactor allows the initiation and sustaining of discharges at atmospheric pressure environments, and in co-existing liquid/vapor media, and offers a high efficiency for the processing of liquid-phase materials. The reactor may be composed of a cylindrical glass chamber, and provided with two stainless-steel upper and bottom caps and a cooling jacket. The rotating, cylindrical, iron, upper electrode is equipped with a quartz jacket to avoid the penetration of the reaction media to the electrode-sustaining central shaft and bearings. The upper electrode has a disc-shaped end terminated in an interchangeable ceramic pin-array and holder. The lower electrode is hollow and has also an interchangeable conical cross-section end piece. In addition, the lower electrode is provided with channels for the re-circulation of the reaction medium. Both the spirally located pin-array and the interchangeable metallic part of the lower electrode can be made of different metals, as required by the specific plasma treatment. In this case, for the synthesis of iron-based carbon nanoparticles, both the spirally located pin-array and the interchangeable metallic part of the lower electrode are made of iron. The distance between the pin-array and the lower electrode can be varied by a micrometric (thimble) screw system.

The reactor is vacuum tight, sealed with copper gaskets; and the rotation of the upper electrode is assured through a magnetic coupling system. The reactor can be operated in a batch-type or continuous flow mode, depending on the specific application. The rotation of the upper electrode is digitally controlled in the range of 0-5000 rpm. The plasma (multitude of spark discharges) can be initiated and sustained using adjustable and commercially available DC or AC power supplies.

Although the actual mechanism for electron emission and energy transport through the liquid is not well characterized at this time, the rotation of the electrode and the spirally arranged pin-array system (which acts as a high-current-density field emission arc source) will generate, under DC or AC voltage conditions, many micro discharges covering the whole area of the electrode surfaces. Rotating the electrode serves several important purposes. The action spatially homogenizes the multiple micro-arcs, activating a larger effective volume of fluid. Spinning the electrode also simultaneously pumps fresh liquid and vapors into the discharge zone, and thins the boundary layer between the emission tips and the bulk liquid.

Reactive or inert gases can also be introduced into the reaction media during the plasma process, through the hollow, lower electrode. The simultaneous presence of a gas environment contributes to the homogenization of the reaction and enhances the micro-arc-formation process due to the lowered density of the medium on the back side of the electrode tip. The individual arc-lets, under spin, sweep out a cylindrical shell volume of plasma while simultaneously pumping fresh fluid into the wake of its filament reaction zone, thus thinning the diffusive boundary layer and enhancing mobility of free radicals into the bulk. The reactor is vacuum-tight, even if it is operated under atmospheric pressure condition. This allows the processing of liquid- and gas-phase toxic media.

During a typical plasma synthesis of the carbon nanoparticles, 200 ml of benzene is introduced into the DMP reactor and argon is injected through the hollow, lower electrode at a pre-selected flow rate. The cooling of the reaction medium is started by flowing tap water through the cooling jacket, and the rotation of the upper electrode is started at the desired angular speed. The discharge is initiated by applying DC voltage on the electrodes, and the plasma-state is sustained for the pre-selected treatment time. The following experimental conditions were employed during the synthesis of nanoparticle systems: Type of electrode: iron; DC voltage: 200 V; current: 1 A; angular speed of the rotating electrode: 1000 rpm; plasma gas: Ar; flow rate of argon: 3 seem; temperature of the reaction media: 18° C.; treatment time: 3 min.

The CMNP/benzene suspension may be separated by using 30-mL Teflon centrifuge tubes and a Fischer Scientific Marathon 22K centrifuge at 3000 rpm for 15 min. The supernatant is then removed with the help of a pipette and the remaining carbon particles is mixed with 25 ml fresh benzene, stirred, and then centrifuged again to wash away soluble byproducts resulting from the DMP treatment. This washing process is repeated 4-6 times until the separated benzene solution turns from brown yellow to colorless. The resulting CMNP are dried in a vacuum oven at 50° C. for at least 24 h. ESCA, FT-IR, SEM, ICP-MS and TG/DTG analytical techniques may used to characterize the properties of the carbon/iron-based magnetic nanoparticles.

Example 2

Immobilization of Biomolecules on Carbon Nanoparticles

This example describes glutaraldehyde-mediated covalent coupling for the immobilization of biomolecules on carbon nanoparticles. The CMNP substrates were activated first by generating aldehyde groups which then react with the primary amino groups on biomolecules. The following immobilization procedure was developed to bind free biomolecules onto the surfaces of functionalized CMNP particles. Prior to immobilization, the CMNP substrate was washed with 50 ml of deionized water (twice) and 50 ml of 0.1 M pH 7 phosphate buffer. A 2% (weight) solution of glutaric dialdehyde (GD) was prepared by diluting 4 ml of 25% GD solution to 25 ml by using 0.1 M pH 7 phosphate buffer. Approximately 100 mg CMNP substrate and 50 ml of the 2% GD solution were added together into a 50-ml beaker, which was then placed into a water bath (controlled by a Fisher Scientific refrigerated circulator model 3210) and incubated for 2 h at 40° C. During the incubation, the CMNP/GD mixture was constantly mixed with a magnetic stirrer. The GD-coated CMNP substrates were then washed with 50 ml of 0.1 M pH 7 phosphate buffer, filtered, dried, and weighed with a Sartorius BA1 lOS Basic series analytical balance (0.1 mg readability) to determine the amount of CMNP substrate left for the subsequent immobilization.

Follow activation, 2 mg of a given antigen and/or antibody was dissolved in 2.0 mL of coupling buffer solution (0.1 M sodium phosphate, 0.15 M NaCl, pH 7.0). An aliquot (0.5 mL) of the solution was saved for later spectrophotometer measurement to determine concentration. The antigen and/or antibody solution (1.5 mL) was added to the activated and washed nanoparticles contained in a beaker. Five (5) mg of sodium cyanoborohydride was added to the beaker, and the reaction was allowed to proceed for four hours at room temperature. The sample was then centrifuged. The resulting gel was washed extensively with coupling buffer to remove unreacted antigen molecules and sodium cyanoborohydride. The sample was then centrifuged again. The antigen-nanoparticle conjugates were then kept at 4° C. before being analyzed.

Example 3

Biological Activity of Functionalized Nanoparticles by DCs

Magnetic nanoparticles were decorated with hen egg lysozyme (HEL)—a model antigen—and anti-DEC 205 IgG antibody (a DC-targeting antibody) according to the methods described in Example 2 in an antibody/antigen molar ratio of 1:8. A representation of the antigen/antibody-coated nanoparticles is shown in FIG. 1B. Cytofluorometric analysis of the particles before (left panel) and after (right panel) conjugation of the HEL and anti-DEC 205 IgG antibody is shown in FIG. 1A. The data indicate that magnetic nanoparticles were decorated with HEL and IgG, and that most of the particles were conjugated to the biomolecules (FIG. 1A).

Figure 2:
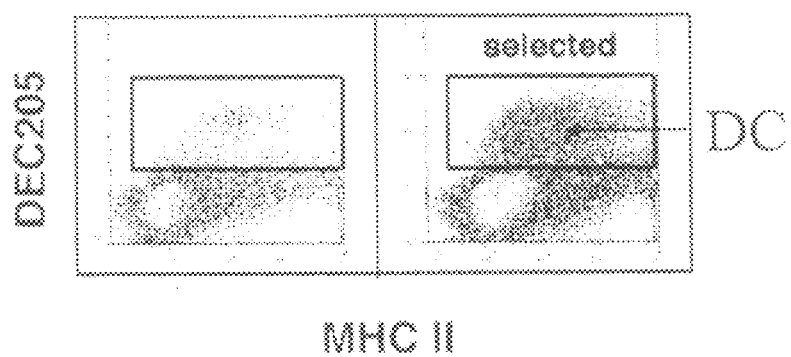
FIG. 2 shows a plot of cytofluorometric analysis of CMNPs that are preferentially taken up by DCs, and selected using a magnet.

Next, the preferential endocytosis of the nanoparticles by DCs was examined. Samples were incubated with nanoparticles prepared as described above. Following incubation, a magnetic field was applied to the sample (a strong permanent magnet) and cytofluorometric analysis was performed. FIG. 2 shows the results of the cytofluorometric analysis. The data indicate that the nanoparticles are taken up selectively by DCs and that the magnetic nanoparticles can be enriched using a localized magnetic field (FIG. 2). As such, the nanoparticle compositions are useful in methods for isolating DCs from a sample.

Figure 3:
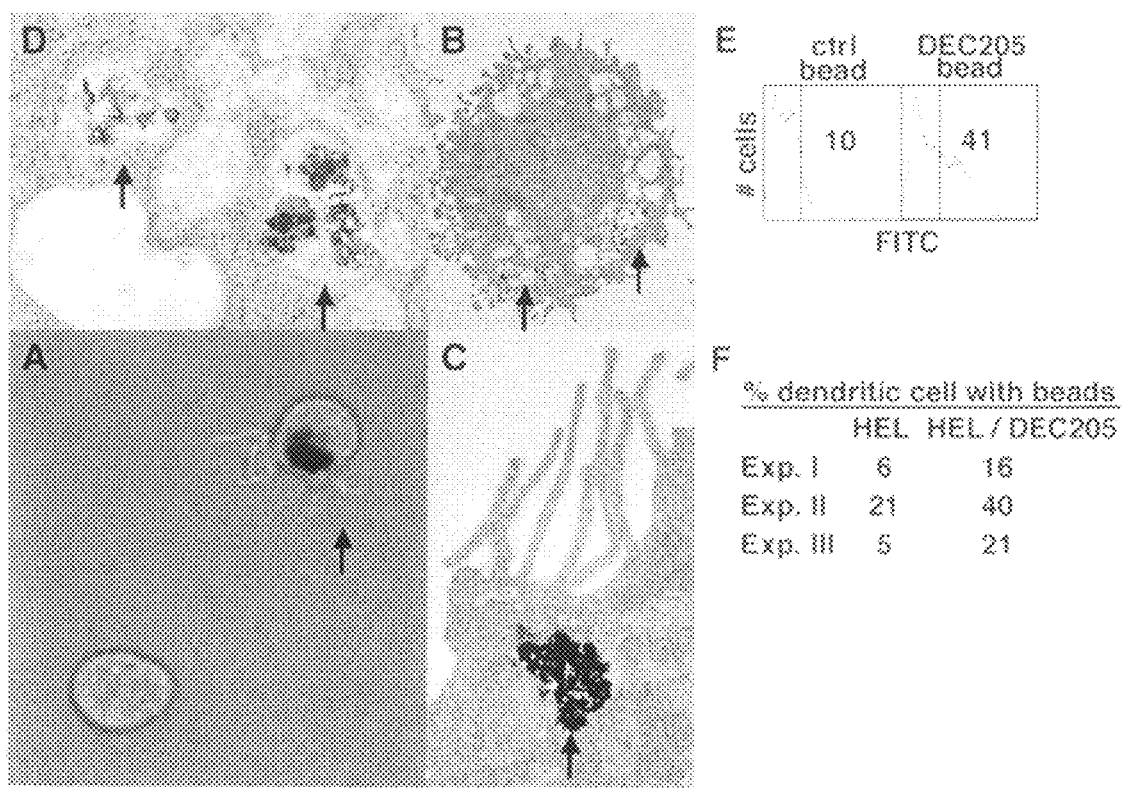
FIG. 3 is a series of micrographs of DCs that have selectively taken up CMNPs, which shows the localization of the CMNPs to the endocytic vesicles.

The localization of the nanoparticles within the DCs was investigated using microscopy. It was shown that the nanoparticles are localized to the endocytic vesicles within the DCs (FIG. 3). Furthermore, it was demonstrated that the anti-DEC 205 antibody on the particle surfaces enhances the particle uptake by DCs (FIG. 3F).

Example 4

T-Cell Activation by Nanoparticle-Exposed DCs

Next, the activation of T cells by DCs that were previously exposed to nanoparticles decorated with a specific antigen was investigated. DCs were incubated with the HEL-decorated nanoparticles as described in Example 2. T cell activation assays were performed using the activated DCs. T cell activation (measured by flow cytometry of activation marker expression) and proliferation (measured by CFSE assay) in response to antigen/antibody dose were plotted.

Figure 4:
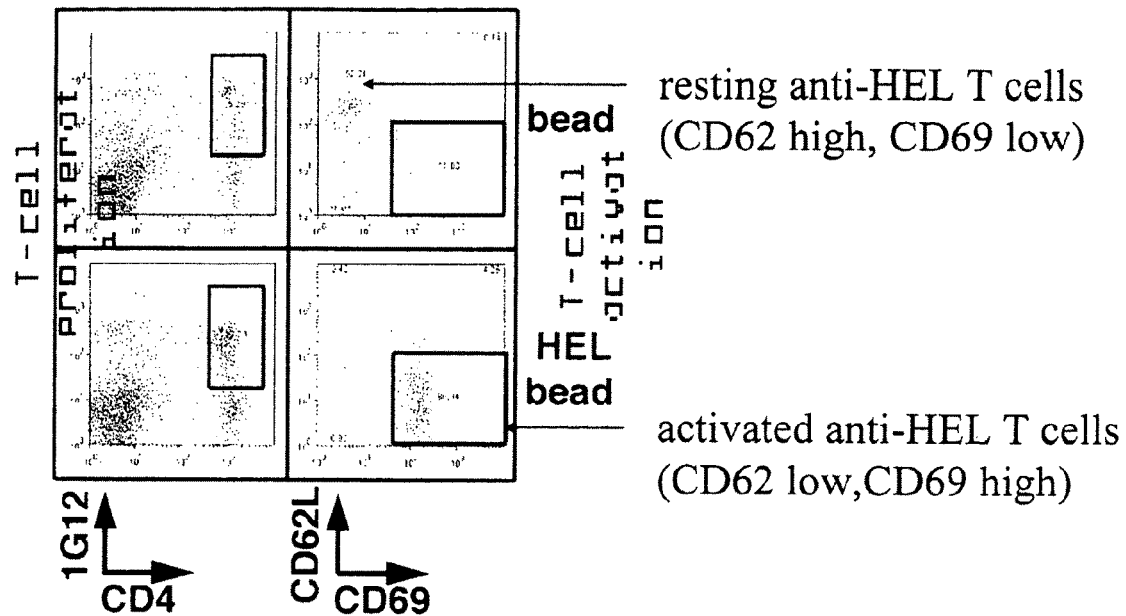
FIG. 4 shows a plot of cytofluorometric analysis of HEL-peptide specific TCR transgenic T cells that are activated by DCs that are treated with HEL-coated CMNPs.

The results indicate that antigenic peptide (HEL)-specific T cell receptor transgenic (CD4+1G12+) T cells were activated by DCs that were previously exposed to nanoparticles decorated with the specific antigen (FIG. 4). By comparing the cytofluorometric data resulting from the resting anti-HEL T cells (CD62 high, CD69 low) and that of the activated (CD62 low, CD69 high) anti-HEL T cells, one can conclude that the antigen-conjugated carbon nanoparticles can induce strong immunity (FIG. 4). As such, the nanoparticle compositions described herein are useful for the activation of DCs ex vivo.

Figure 5:
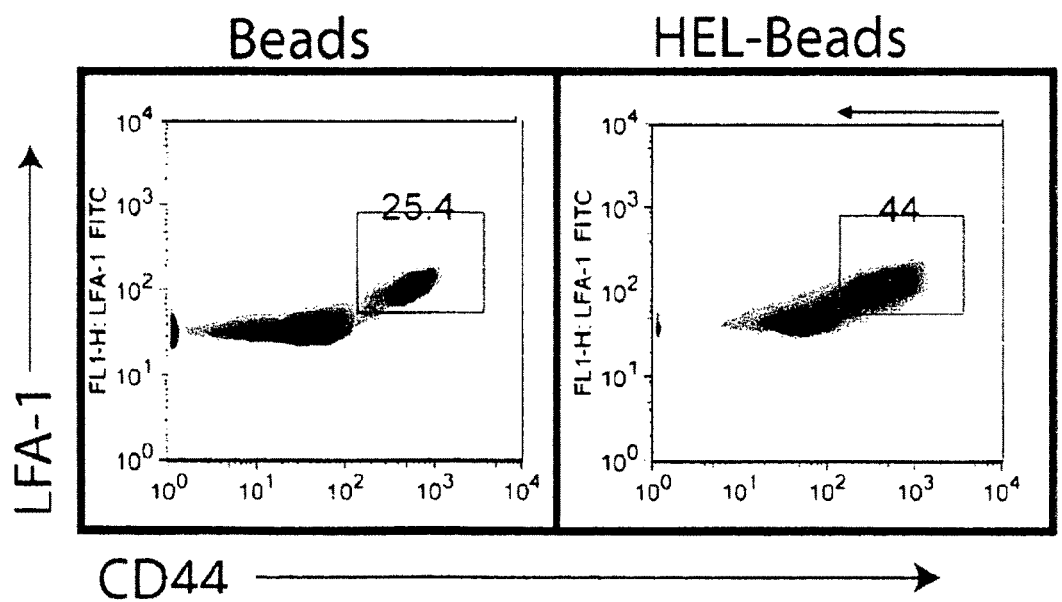
FIG. 5 shows a plot of cytofluorometric analysis of activated anti-HEL T cells (LFA1 high, CD44 high) from mice which were injected with DCs that are treated with HEL-coated CMNPs.

In vivo experiments performed on mice also demonstrate that a carbon nanoparticle-bound antigen system induces a strong immune response. The antigen-conjugated nanoparticles were prepared as described in Example 3 and were injected into mice. The activation of T-cells in vivo was measured. FIG. 5 shows cytofluorometric data which indicate that HEL-peptide-specific TCR transgenic CD4+ T cells are activated by HEL-coated nanoparticles injected in mice. As such, the nanoparticle compositions described herein are useful for methods of inducing an immune response in vivo.

Example 5

Isolating Nanoparticle-Containing DCs from Tissue Samples by Magnetic Separation Due to the magnetic behavior characteristics of nanoparticles synthesized using iron electrodes, targeted, localized delivery of bioactive particle-biomolecular assemblies is also possible. In one experiment, DCs were incubated with the HEL-decorated nanoparticles as described in Example 3. The DCs were then injected into mice and the mice were exposed to a magnetic field at the anterior (FIG. 6A) or posterior (FIG. 6B). Cells were isolated from either cervical lymph nodes or inguinal lymph nodes.

Figure 6:
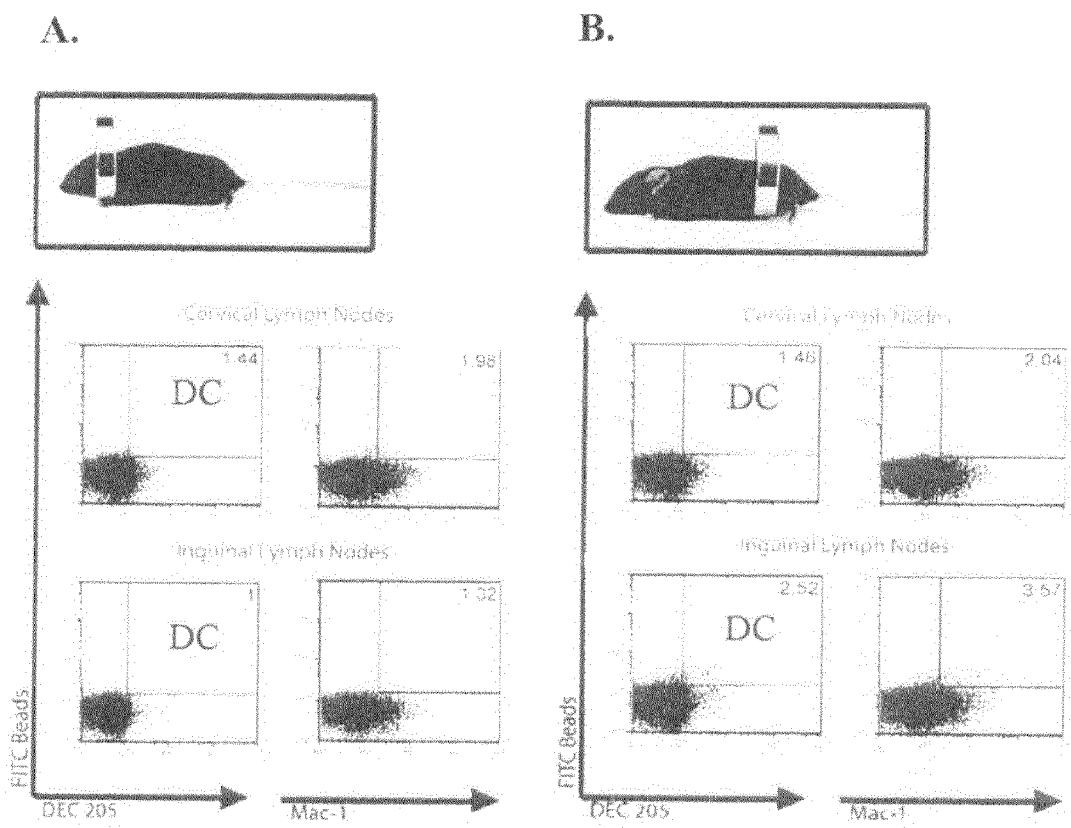
FIG. 6 shows plots of cytofluorometric analysis of lymph node cells from samples where the in vivo traffic of DCs containing endocytosed CMNPs was changed by magnets. DEC-205 is a DC marker; Mac-1 is a macrophage marker; and the carbon beads are labeled with avidin-FITC.

The results are shown in FIG. 6, and indicate that in vivo traffic of cells that endocytosed the magnetic, functionalized (e.g., fluorescence-labeled) nanoparticles can conveniently be controlled by localized magnetic fields. FIG. 6 shows that when antibodies reacting with a complement component receptor (Mac-) or DC marker DEC-205 were used for generating functional nanoparticles, both the DC traffic and the site (location) of the immune response could be controlled using functionalized, magnetic particles. Thus, the magnetic properties of the nanoparticles facilitate their manipulation and detection in vivo. Furthermore, populations of bone marrow cells can be enriched for class II+DEC205+DCs by culturing them in the presence of magnetic nanobeads. Class II+DEC205+DCs can be further isolated from this population by magnetic sorting.

Figure 7:
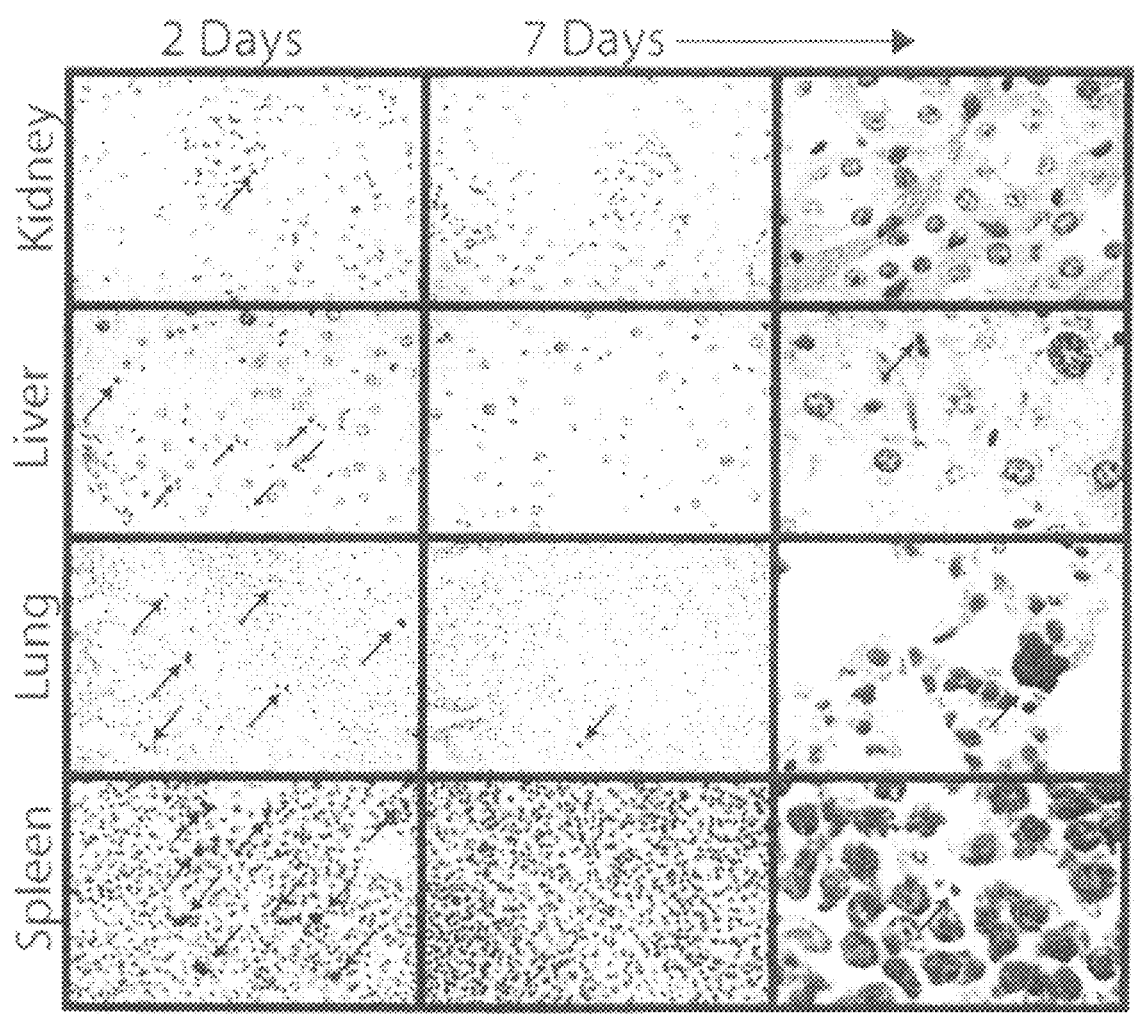
FIG. 7 shows micrographs of the tissue distribution of intravenously injected CMNPs in mice after two days and seven days.

Evaluation of tissue distribution of functionalized and intravenously injected carbon-based nanoparticles in mice was performed. Kidney, liver, lung, and spleen tissues were analyzed by microscopy. The results indicate that, two days after the injection, the extracellular particles were present in the kidney, liver, lung, and spleen (FIG. 7). After seven days, most of the particles were cleared (FIG. 7). Further, it was found that the particles did not induce any inflammation or toxicity even if they were agglomerated within certain tissue areas.

Example 6

Isolation of Nanobead-Labeled DCs from Tissues

Figure 8:
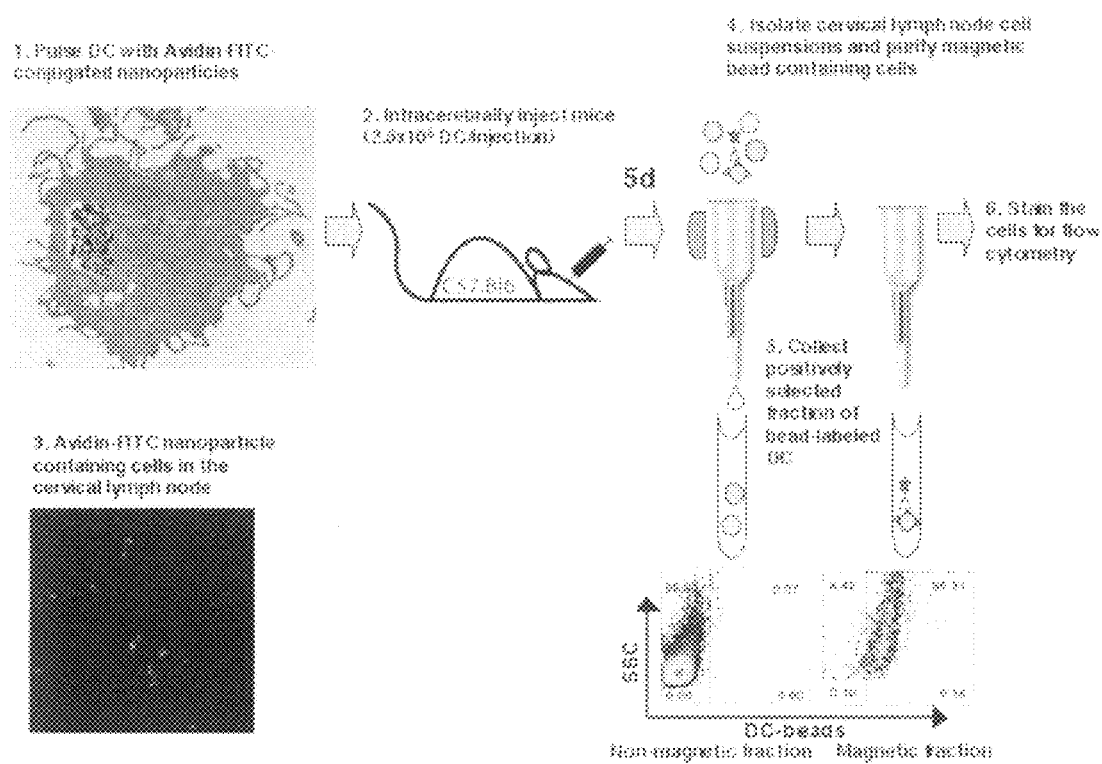
FIG. 8 shows a flow chart of the experimental approach to track the migration of DCs in vivo.

The ability to isolate nanobead-containing DCs from tissue samples by magnetic separation was tested. In this experiment, DCs were pulsed with avidin-FITC conjugated nanoparticles. FIG. 8.1 shows an EM image of in vitro-cultured DCs harboring engulfed nanobeads. In previous studies, it was demonstrated that, following injection into mouse brains, GFP-expressing DCs migrate to the cervical lymph nodes (CLN) and activate T cells, which are in turn recruited to the brain. To determine whether nanobead-labeled DCs function similarly, nanoparticle-containing DCs were injected intracerebrally (2.5×105 DC/injection). Their migration from the CNS to the CLN was tracked (FIG. 8.2). As shown in FIG. 8.3, fluorescent nanoparticle-containing DCs can be detected in the cervical lymph node (CLN) five days after injection. When single cell suspensions derived from CLN were applied to magnetic columns, no fluorescent cells were detected in the non-magnetic fraction. In contrast, most of the cells in the magnetic fraction were fluorescent (FIG. 8, FACS). Importantly, flow cytometry analysis of these cell populations using antibodies specific for DC markers (DEC205, CD11c) demonstrates that >90% of the cells recovered in the magnetic fraction were DCs. First, these data show that, in vivo, the magnetic nanobeads are nontoxic and nanobead-containing DCs survived long enough to induce T cell responses. Second, the ability to isolate and phenotype nanoparticle-containing cells provides a feasible method to determine the phenotype and function of DC subtypes in various tissues.

Example 7

Isolation of DC from *Mycobacterium*-Induced Inflammatory Lesions

Figure 9:
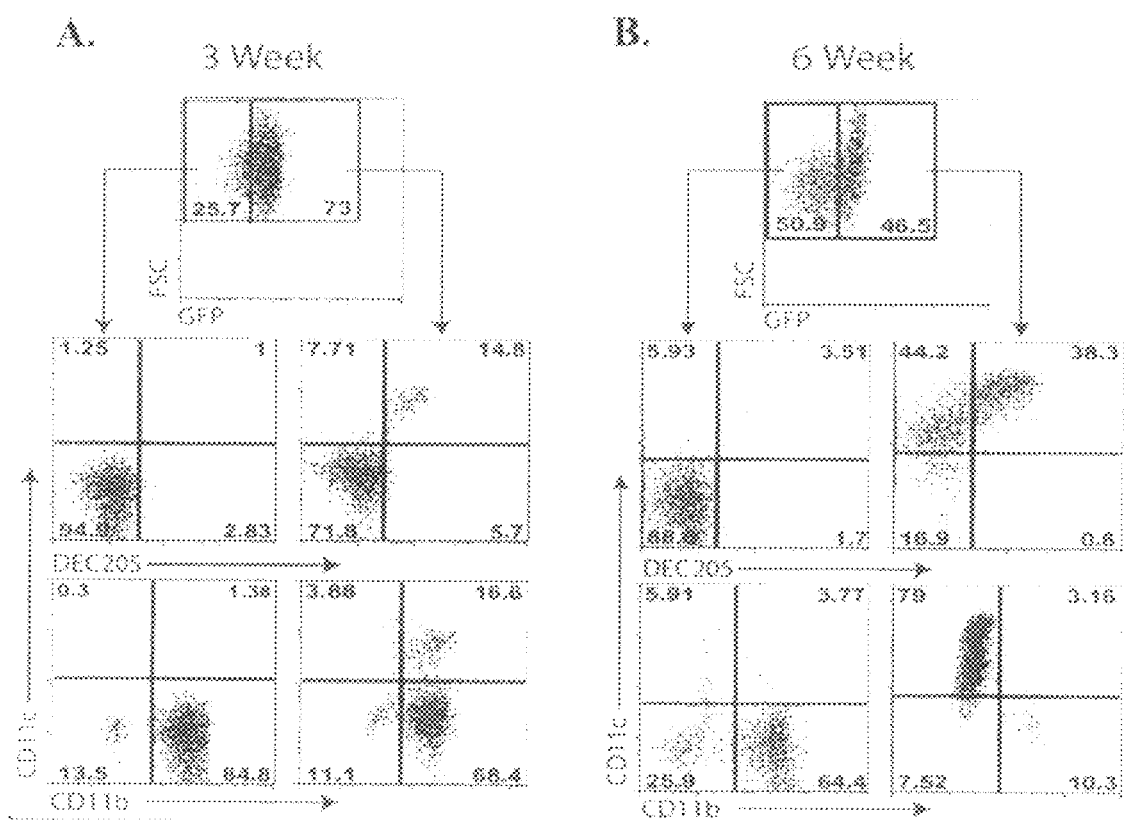
FIG. 9 shows plots of cytofluorometric analysis of granuloma cells from *Mycobacterium* infected mice that were injected with fluorescent CMNPs. The cells were subjected to magnetic separation.

The hallmark of mycobacterial infection is granuloma formation. This inflammatory site is where the bacteria survive during chronic inflammation. *Mycobacterium*-infected animals were injected 3 or 6 weeks after the infection with fluorescent carbon nanobeads. Liver granulomas were isolated and single-cell suspensions were prepared. The cells were subjected to magnetic separation and a large part of the cells were fluorescent, indicating that they contained the fluorescent nanobeads. Upon further analysis using antibodies recognizing DC surface molecules CD11c and DEC 206, it was shown that a large portion of cells were in fact DCs. In the case of 6-week granulomas, DCs were enriched from 2-3% to more than 70% (FIG. 9).

Example 8

Figure 10:
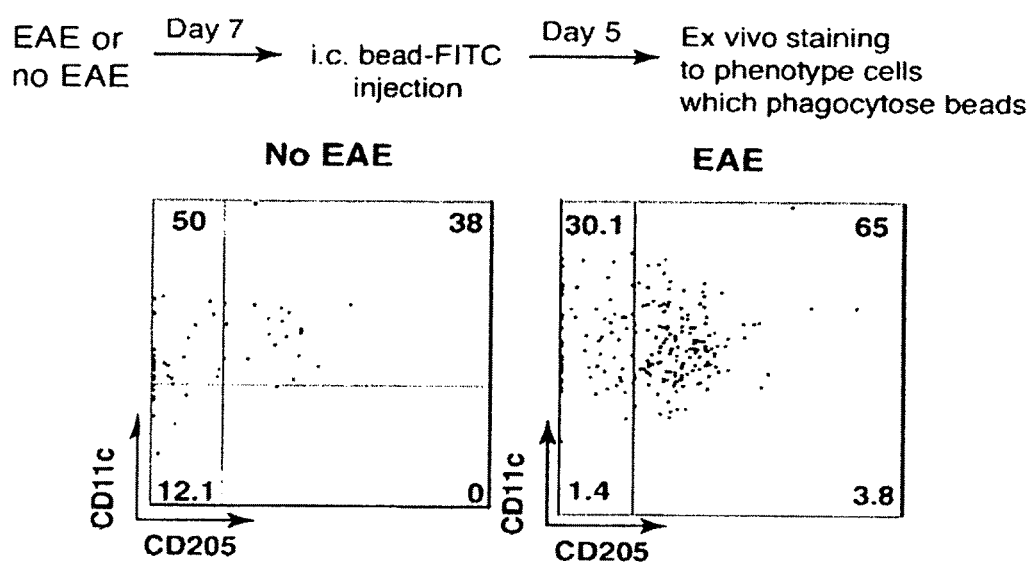
FIG. 10 shows the accumulation of nanobead positive DCs in the brain during Experimental Autoimmune Encephalomyelitis (EAE).

Nanobead Isolation of DCs from Tissues to Analyze Kinetic Distribution in Autoimmune Diseases of the Central Nervous System Avidin-FITC-conjugated nanobeads were delivered intercerebrally seven days following induction of autoimmune disease. Five days later, leukocytes were isolated from the brain and nanobead-containing cells were analyzed. Data are shown in FIG. 10 and reveal a significant accumulation of CD11c+CD205+DCs in the brain at this time point. Using this method, nanobead-containing DCs can be isolated to analyze the phenotypic and functional characteristics of these cells at various time points during brain inflammatory diseases.

Thus, it should be understood that, although the present invention has been specifically disclosed by preferred embodiments and optional features, modifications, improvements and variations of the inventions embodied and herein disclosed may be made by those skilled in the art, and that such modifications, improvements and variations are considered to be within the scope of this invention. The materials, methods, and examples provided here are representative of preferred embodiments, are exemplary, and are not intended as limitations on the scope of the invention.

In addition, where features or aspects of the invention are described in terms of Markush groups, those skilled in the art will recognize that the invention is also thereby described in terms of any individual member or subgroup of members of the Markush group.

Other embodiments are set forth within the following claims.

What is claimed is:

1. A vaccine delivery system comprising: a carbon nanoparticle that is preferentially endocytosed by dendritic cells as compared to macrophages; and an antigenic protein or peptide conjugated to the nanoparticle, wherein the carbon nanoparticle is spherical and has a diameter of about 30 nm to about 70 nm, and wherein the carbon nanoparticle comprises iron, wherein the iron concentration of the nanoparticle is from 0.5% to 2.0%; wherein the antigenic protein or peptide induces an immune response comprising the production of antibodies specific for the antigenic protein or peptide; and wherein the nanoparticle is conjugated to an antibody capable of binding specifically to molecules on the surface of dendritic cells.

2. The vaccine delivery system of claim 1, wherein the carbon nanoparticle is a magnetic carbon nanoparticle.

3. The vaccine delivery system of claim 2, wherein the magnetic carbon nanoparticle comprises iron, and wherein the iron concentration of the nanoparticle is from about 0.5% to 1.0%.

4. The vaccine delivery system of claim 1, wherein the antibody specifically binds to molecules selected from the group consisting of: DC-SIGN, DEC-205, and mannose receptor.

5. The vaccine delivery system of claim 1, wherein the antigen is associated with an infectious disease.

6. The vaccine delivery system of claim 5, wherein the infectious disease is caused by a pathogenic microorganism selected from the group consisting of a virus, a bacterium, a fungus and a protozoan.

7. The vaccine delivery system of claim 1, wherein the antigen is encoded by a viral gene.

8. The vaccine delivery system of claim 7, wherein the viral gene is derived from a virus selected from the group consisting of a hepatitis B virus, a hepatitis C virus, a human immunodeficiency virus, a papillomavirus, and a herpes virus.

9. The vaccine delivery system of claim 8, wherein the antigen is encoded by a viral gene selected from the group consisting of a hepatitis B virus e antigen gene, a hepatitis B virus surface antigen gene, a hepatitis B virus core antigen gene, human immunodeficiency virus Env gp160 gene, Gag gene, Pol gene, Rev gene, Tat gene, Vif gene, and Nef gene.

10. The vaccine delivery system of claim 1, wherein said antigenic protein or peptide is a tumor-associated antigen selected from the group consisting of an overexpressed tumor-associated antigen, a testis-tumor antigen, a mutated tumor-associated antigen, a differentiation tumor-associated antigen tyrosinase, BCR-ABL, CASP, CDK, Ras, p53, HER-2/neu, CEA, MUC, TW1, PAP, survivin, telomerase, EGFR, PSMA, PSA, PSCA, tyrosinase, MART, TRP, gp100, MART, MAGE, BAGE, GAGE, LAGE/NY-ESO, RAGE, SSX-2, CD19, and CD20.

11. The vaccine delivery system of claim 1, wherein the antigenic protein or peptide is conjugated to the nanoparticle via an amine functionality.

12. A method for inducing an immune response in a mammalian subject comprising administering to the subject the vaccine delivery system of claim 1.

13. The method of claim 12, wherein the vaccine delivery system is administered subcutaneously or intravenously.

14. The method of claim 12, further comprising the step of directing the nanoparticles to a specific site in the subject using a magnet.

* * * * *